United States Patent
Porro et al.

(10) Patent No.: US 11,697,831 B2
(45) Date of Patent: Jul. 11, 2023

(54) CELL ABLE TO PRODUCE POLY L-LACTIC ACID

(71) Applicants: UNIVERSITÀ DEGLI STUDI DI MILANO—BICOCCA, Milan (IT); GALATEA BIOTECH S.R.L., Milan (IT)

(72) Inventors: Danilo Porro, Cernusco sul Naviglio (IT); Paola Branduardi, Milan (IT); Stefano Bertacchi, Milan (IT); Nadia Maria Berterame, Milan (IT)

(73) Assignees: UNIVERSITÀ DEGLI STUDI DI MILANO-BICOCCA, Milan (IT); GALATEA BIOTECH S.R.L., Milan (IT)

( * ) Notice: Subject to any disclaimer, the term of this patent is extended or adjusted under 35 U.S.C. 154(b) by 0 days.

(21) Appl. No.: 17/265,135

(22) PCT Filed: Jul. 31, 2019

(86) PCT No.: PCT/EP2019/070665
§ 371 (c)(1),
(2) Date: Feb. 1, 2021

(87) PCT Pub. No.: WO2020/025694
PCT Pub. Date: Feb. 6, 2020

(65) Prior Publication Data
US 2021/0324429 A1    Oct. 21, 2021

(30) Foreign Application Priority Data
Aug. 3, 2018 (IT) .................. 102018000007846

(51) Int. Cl.
*C12P 7/625* (2022.01)
*C12N 9/04* (2006.01)
*C12N 9/10* (2006.01)

(52) U.S. Cl.
CPC ............ *C12P 7/625* (2013.01); *C12N 9/0006* (2013.01); *C12N 9/1029* (2013.01); *C12Y 101/01027* (2013.01); *C12Y 208/03001* (2013.01)

(58) Field of Classification Search
CPC ..... C12P 7/625; C12N 9/0006; C12N 9/1029; C12N 9/13; C12N 1/18; C12Y 101/01027; C12Y 208/03001; C12Y 203/01
See application file for complete search history.

(56) References Cited

U.S. PATENT DOCUMENTS 9,120,891 B2   9/2015 Lee et al.

FOREIGN PATENT DOCUMENTS

| EP | 2 314 638 | 4/2011 |
|----|-----------|--------|
| WO | 2006/126796 | 11/2006 |
| WO | 2009/022797 | 2/2009 |
| WO | 2017/108577 | 6/2017 |

OTHER PUBLICATIONS

Witkowski et al., Biochemistry 38:11643-11650, 1999.*
Tang et al., Phil Trans R Soc B 368:20120318, 1-10, 2013.*
Seffemick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Colombié et al., Enzyme and Microbial Technology 33:38-46, 2003.*
Ferain et al., GenBank accession No. CAA50277, published Apr. 18, 2005.*
Valentin et al., Applied Microbiology and Biotehcnology 40:699-709, 1994.*
Solaiman, D., GenBank accession No. AAD26365, published Jul. 14, 2016.*
Selmer et al., GenBank accession No. CAB77204, published Jul. 26, 2016.*
Branduardi et al., "Lactate production yield from engineered yeasts is dependent from the host background, the actate dehydrogenase source and the lactate export", Microbial Cell Factories, Jan. 30, 2006, vol. 5, No. 4, 12 pages.
Braunegg et al., "A Rapid Gas Chromatographic Method for the Determination of Poly-β-hydroxybutyric Acid in Microbial Biomass", European Journal of Applied Microbiology and Biotechnology, Mar. 1978, pp. 29-37.
Castaño-Cerezo et al., "An insight into the role of phosphotransacetylase (pta) and the acetate/acetyl—CoA node in *Escherichia coli*", Microbial Cell Factories, Oct. 24, 2009, vol. 8, No. 54, 19 pages.
Chen et al., "Plastics Derived from Biological Sources: Present and Future: A Technical and Environmental Review", Chemical Reviews, Dec. 21, 2011, vol. 112, No. 4, pp. 2082-2099.
Choi et al., "Use of waste Chinese cabbage as a substrate for yeast biomass production", Bioresource Technology, Jul. 2002, pp. 251-253.
Choi et al., "One-step fermentative production of poly(lactate-co-glycolate) from carbohydrates in *Escherichia coli*", Nature Biotechnology, Mar. 7, 2016, vol. 34, No. 4, pp. 435-440.
Garlotta, "A Literature Review of Poly(Lactic Acid)", Journal of Polymers and the Environment, Apr. 2001, vol. 9, No. 2, pp. 63-84.
Goldberg, "PDLA a potential new potent topical analgesic: a case report", Local and Regional Anesthesia, Oct. 24, 2014, vol. 2014, No. 7, pp. 59-61.

(Continued)

*Primary Examiner* — Delia M Ramirez
(74) *Attorney, Agent, or Firm* — Nixon & Vanderhye

(57) ABSTRACT

Disclosed is the production by fermentation of poly D-lactic acid (PDLA) and poly L-lactic acid (PLLA). In particular, there is provided engineered (prokaryotic or eukaryotic) cells for the direct synthesis of PLLA polymers and engineered eukaryotic cells for the direct synthesis of PDLA polymers starting from a carbon source, including residual biomasses of the different production chains.

12 Claims, 12 Drawing Sheets

Specification includes a Sequence Listing.

(56) References Cited

OTHER PUBLICATIONS

Gorenflo et al., "Quantification of bacterial polyhydroxyalkanoic acids by Nile red staining", Applied Microbiology and Biotechnology, Jun. 1999, vol. 51, pp. 765-772.
Jamshidian et al., "Poly-Lactic Acid: Production, Applications, Nanocomposites, and Release Studies", Comprehensive Reviews in Food Science and Food Safety, Sep. 2010, vol. 9, pp. 552-571.
Jansen et al., "Saccharomyces cerevisiae strains for second-generation ethanol production: from academic exploration to industrial implementation", FEMS Yeast Research, Aug. 2017, vol. 17, No. 5, 20 pages.
Jung et al., "Metabolic Engineering of Escherichia coli for the Production of Polylactic Acid and Its Copolymers", Biotechnology and Bioengineering, Jan. 1, 2010, vol. 105, No. 1, pp. 161-171.
Kumar et al., "Methods for Pretreatment of Lignocellulosic Biomass for Efficient Hydrolysis and Biofuel Production", Industrial & Engineering Chemistry Research, Mar. 20, 2009, vol. 48, No. 8, pp. 3713-3729.
Li et al., "Application of synthetic biology for production of chemicals in yeast Saccharomyces cerevisiae", FEMS Yeast Research, Jan. 6, 2015, vol. 15, Issue 1, 12 pages.
Maillard et al., "Differences Between Crystals Obtained in PLLA-Rich or PDLA-Rich Stereocomplex Mixtures", Macromolecules, Apr. 7, 2010, vol. 43, No. 9, pp. 4006-4010.
Marcó et al., "Bacteriophages and dairy fermentations", Bacteriophage, Jul. 1, 2012, vol. 2, No. 3, pp. 149-158.
Mathuriya et al., "Polyhydroxyalkanoates: Biodegradable Plastics and Their Applications", Handbook of Ecomaterials, Jan. 2017, 29 pages.
Mukherjee et al., "Membrane localization and dynamics of Nile Red: Effect of cholesterol", Biochimica et Biophysica Acta (BBA)—Biomembranes, Jan. 2007, vol. 1768, Issue 1, pp. 59-66.
Okano et al., "Biotechnological production of enantiomeric pure lactic acid from renewable resources: recent achievements, perspectives, and limits", Applied Microbiology and Biotechnology, Oct. 14, 2009, vol. 85, No. 3, pp. 413-423.
Porro et al., "Production of recombinant proteins and metabolites in yeasts: when are these systems better than bacterial production systems?", Applied Microbiology and Biotechnology, Dec. 2, 2010, vol. 89, No. 4, pp. 939-948.
Rasal et al., "Poly(lactic acid) modifications", Progress in Polymer Science, Mar. 2010, vol. 35, Issue 3, pp. 338-356.
Schweiger et al., "On the dehydration of (R)-lactate in the fermentation of alanine to propionate by Clostridium propionicum", FEBS Letters, Jun. 1984, vol. 171, No. 1, pp. 79-84.
Soares et al., "Fed-batch production of green coconut hydrolysates for high-gravity second-generation bioethanol fermentation with cellulosic yeast", Bioresource Technology, Jul. 27, 2017, vol. 244, pp. 234 242.
Spiekermann et al., "A sensitive, viable-colony staining method using Nile Red for direct screening of bacteria that accumulate polyhydroxyalkanoic acids and other lipid storage compounds", Archives of Microbiology, Feb. 1999, vol. 171, pp. 73-80.
Auras et al., "Poly(lactic acid): Synthesis, Structures, Properties, Processing, and Applications", Wiley Series on Polymer Engineering and Technology, Oct. 2010, 22 pages.
Xiao et al., "Poly(Lactic Acid)-Based Biomaterials: Synthesis, Modification and Applications", Engineering, Jan. 20, 2012, Biomedical Science, Engineering and Technology, pp. 247-282.
Yang et al., "Biosynthesis of polylactic acid and its copolymers using evolved propionate CoA transferase and PHA synthase", Biotechnology and Bioengineering, Jan. 1, 2010, vol. 105, No. 1, pp. 150-160.
Yang et al., "Tailor-made type II Pseudomonas PHA synthases and their use for the biosynthesis of polylactic acid and its copolymer in recombinant Escherichia coli", Appl.Microbiol.Biotechnol., Jan. 11, 2011, vol. 90, pp. 603-614.
International Search Report for PCT/EP2019/070665 dated Sep. 9, 2019, 4 pages.
Written Opinion of the ISA for PCT/EP2019/070665 dated Sep. 9, 2019, 5 pages.

* cited by examiner

CELL ABLE TO PRODUCE POLY L-LACTIC ACID

CROSS-REFERENCE TO RELATED APPLICATIONS

This application is the U.S. national phase of International Application No. PCT/EP2019/070665 filed Jul. 31, 2019 which designated the U.S. and claims priority to IT 102018000007846 filed Aug. 3, 2018, the entire contents of each of which are hereby incorporated by reference.

REFERENCE TO SEQUENCE LISTING SUBMITTED ELECTRONICALLY

The content of the electronically submitted sequence listing (Name: 7526-79_SEQ_LISTING.txt; Size: 9.83 kilobytes; and Date of Creation: Feb. 1, 2021) filed with the application is incorporated herein by reference in its entirety.

BACKGROUND OF THE INVENTION

Field of the Invention

The present invention relates to a process for the production by direct fermentation of poly L-lactic acid (PLLA) from a carbon source by engineered prokaryotic or eukaryotic cells or of poly D-lactic acid (PDLA) from sugars by engineered eukaryotic cells. The invention also refers to cells having a metabolic flow redirected for the synthesis of enantiomerically pure polymers such as PDLA or PLLA starting from a carbon source, which preferably derives from residual biomasses of production chains.

Description of the Related Art

Polylactic acid (PLA) is a biodegradable biopolymer derived from lactic acid. Due to its chemical-physical properties, it is an unbranched aliphatic polyester, belonging to the class of thermoplastic polymers. Because of its characteristics, PLA is very similar to polyethylene terephthalate (PET), a common plastic used mainly for food packaging. PET has a petrochemical derivation, while PLA is obtained from the polymerization of lactic acid, obtained in turn by fermentation (Jamshidian et al., 2010; Tsuji et al., 2011). The need to avoid processes based on the use of oil, a fossil resource that is depleting due to rapid human consumption, in favor of bio-based systems, is driving several companies to use bioplastics.

There are several applications of PLA in many sectors, such as: the food sector (packaging, plates, cutlery, glasses, bottles, among others), 3D printing, where it can replace acrylonitrile butadiene styrene (ABS), and the medical field (e.g. biocompatible suture threads, capsules for drug delivery, among others) (Garlotta, 2001; Rasal et al., 2010; Xiao et al., 2012). The versatility of the PLA allows the printing of finished products both in extrusion and in injection, and, remarkably, it is possible to use the machineries and infrastructures already developed for PET (Jamshidian et al., 2010).

PLA can be stained by masterbatch and mixed with other plastics (biodegradable or not, of petrochemical derivation or not), in order to obtain compounds with new properties. In addition, it is possible to find the PLA in co-polymer form, in which lactic acid monomers alternate with other hydroxy acids such as 3-hydroxybutyrate (3HB) or glycolate (Choi et al., 2016; Xiao et al., 2012; Tsuji et al., 2010).

PLA, differently from traditional plastics like PET, is biodegradable in the environment and biocompostable, namely disposable among organic waste. Therefore, a PLA object-product, once its life cycle has ended, is reabsorbed by the soil, favoring the formation of new biomass that can be further used for the production of PLA (Tsuji et al., 2011; Chen and Patel, 2012). As a consequence, the PLA has a circular supply chain thanks to both its origin from renewable biomasses and its intrinsic biodegradability.

The global PLA market (about 210 thousand tons/year in 2017) is growing steadily and production is expected to increase by 50% by 2022 compared to that recorded in 2017 (see website at european-bioplastics.org). There are three types of PLA depending on the enantiomeric forms of the constituent monomers: PLLA composed of only L-lactic acid monomers, the PDLA consisting of only D-lactic acid monomers, and PDLLA consisting of a mixture of both monomers (Jamshidian et al., 2010; Tsuji et al., 2011). PDLA and PLLA are in a semi-crystalline form, while PDLLA in amorphous form (Tsuji et al., 2011). The chirality of the monomers constituting the PLA is transferred to the polymer itself (hence PDLA or PLLA), which acquires precise chirality. This leads, in the solid form, in a different interaction between adjacent first chains and in a possible lamellar or crystalline structure peculiar to the two single enantiomers, which can preserve, at least partially, chirality. In particular, even in the form of a thin film, PDLA or PLLA can present morphology and at least partial chirality of surfaces, peculiar to the specific enantiomer (Maillard and Prud'homme, 2010), showing phenomena of circular dichroism.

However, considering the chemical-physical characteristics, these polymers are very similar to each other, for example they are soluble in the same organic solvents (e.g. benzene, chloroform, acetonitrile, etc.). Furthermore, there are no significant differences in terms of melting temperature (Tm~180° C.), decomposition temperature (~200° C.), and elongation (20-30%) (Xiao et al., 2012), which mainly depend on the molecular weight of the polymer. From a commercial point of view, the market is dominated by PLLA, which is mainly used for the production of disposable objects. The PDLA has instead a more niche market and applications in the medical field, since, for instance, it may have two beneficial effects for wound healing: (i) providing a protective barrier as a hydrogel; and (ii) serving as an analgesic by sequestering lactate (Goldberg, 2014).

Traditionally, PLA (in its enantiomerically pure and non-pure forms) is produced by a chemical synthesis, starting from the lactic acid obtained by fermentation. Unlike other bioplastics, such as polyhydroxyalkanoates (PHA), no known natural organisms are able to directly synthetize PLA (Chen and Patel, 2012). The industrial production of PLA occurs mainly through a ring-opening polymerization, by means of a cyclic intermediate, called lactide, capable of facilitating the reaction. However, this chemical process has aspects that reduce the environmental sustainability of this bioplastic: (i) to complete the polymerization it is necessary to use stannic octanoate as a catalyst and (ii) to allow chemical polymerization it is necessary that lactic acid is in its protonated form, and not in the form of lactate (Garlotta, 2001; Jamshidian et al., 2010; Rasal et al., 2010; Tsuji et al., 2011). However, since the main supply chains of PLA involve the use of lactic acid bacteria, it becomes necessary to treat the final fermentation product with high amounts of acid. In fact, to allow the growth of these organisms it is necessary to maintain constant the pH of the culture broth around a value of 5 (Okano et al., 2010). Since the $pK_a$ of lactic acid is 3.86, under these conditions, the final product is lactate. Consequently, acidification at the end of the fermentation is necessary, as previously mentioned. Moreover, the nutritional needs of lactobacilli are in most cases complex: this determines the need for rich media formulations which are rarely compatible with the use of residual biomasses as a growth substrate. Even more important, this often determines a greater complexity in downstream purification of the desired monomer (Okano et al., 2010). Finally, the lactobacilli, unlike yeasts, are subject to attack by bacteriophages during the fermentation process (Marco et al., 2012). The use of yeasts is a valid alternative, since many species belonging to this group, for instance the baker's yeast *Saccharomyces cerevisiae*, are able to grow in soils characterized by low pH values, even lower than a value of 3. Yeasts are unicellular microorganisms widely used by the bioindustry. In particular, *S. cerevisiae* is the eukaryotic microorganism best known at the molecular, genetic and biochemical level and has the status of GRAS (Generally Recognized As Safe) microorganism (Porro et al., 2011; Li and Borodina, 2015). Furthermore, compared to bacteria such as lactobacilli, yeasts have less complex nutritional requirements that allow their growth on residual biomasses as reported, as a simple sake of example, by Soares et al., (2017), Jansen et al., (2017) and Choi et al., (2002).

Although lactic acid fermentation already represents a sustainable step forward for the production of bioplastics compared to the oil-based production, aiming to further reduce the impact of the conventional process based on chemical polymerization, the direct microbiological synthesis represents an ideal solution. As previously mentioned, in nature no known organisms are able to accumulate polylactic acid. Instead, unlike eukaryotes, many prokaryotes are however able to produce aliphatic polyesters as reserve polymers. Therefore, the development and use of eukaryotic cells for the production of polylactic acid require a deep and new engineering.

SUMMARY OF THE INVENTION

The present invention relates to a method for the complete—one-step—biological synthesis of PDLA and/or PLLA, and eukaryotic cells engineered for this purpose. Both biosyntheses include the bioconversion of a carbon source in PDLA and/or PLLA. The metabolic pathways of this invention include the bioconversion of pyruvate to lactate, followed by its activation with a CoA donor, preferably acetyl-CoA, to lactyl-CoA and subsequent polymerization to PDLA and/or PLLA.

Examples of eukaryotic cells capable of producing PDLA have been already described by Dusseaux et al. (WO2017/108577). However, this approach is quite complex. Indeed, this approach requires the addition of lactic acid to the medium for the production of PDLA and the development of a two phase process. Therefore, lactic acid must be produced by a different cell factory and/or by chemical synthesis. In this respect, lactic acid should be considered as a mandatory substrate and not like an intermediate product (which is the case for the invention here disclosed, see below). Being a substrate, the ability to consume lactic acid as carbon source need to be attenuated or eliminated. Furthermore, this approach also requires methods to increase the productivity of intracellular Coenzyme A (CoA) donor. This goal can be obtained by facilitating the accumulation of intracellular CoA donor and/or by disrupting the pathway(s) using CoA.

Surprisingly, despite the wider industrial application of PLLA and the many research skills related to the production of PDLA, no examples of prokaryotic or eukaryotic cells capable of producing PLLA have never been described.

In order to verify the insertion of a metabolic pathway that allows the conversion of carbon source, preferably glucose, into PDLA and/or PLLA, different experiments were performed using engineered yeast strains showing the production of these polymers (see Examples 8-10). FIG. 5A and FIG. 5B show a detailed scheme of the synthetic pathway of PDLA and/or PLLA starting from glucose, transformed in yeast cells by the inventors of the present invention.

In literature there are examples of genetic modifications of the bacterium *Escherichia coli*, in order to directly produce pure PDLA or in the form of co-polymer with 3-HB or other monomers (Cho et al., WO2006/126796; Jung et al., 2010; Yang et al., 2010; Choi et al., 2016). However, the use of *E. coli* has two main limitations: (i) during the fermentation process, the aforementioned microorganism may be subject to attack by bacteriophages, unlike eukaryotic cells (Marco et al., 2012) and (ii) the metabolism of *E. coli* is characterized by a mixed acid fermentation in which lactic acid is not the sole fermentation product, with consequent effects on the production yield of the metabolite of interest (Castaño-Cerezo et al., 2009). Remarkably, these examples refer to the incorporation of lactic acid only in the enantiomeric form D, while there are no examples of direct PLLA synthesis, or incorporation of L-lactic acid monomers within the biopolymers produced. This is related to the fact that the system based on *E. coli* exploits the natural ability of the bacterium to produce only lactic acid in the enantiomeric form D. Conversely, the cell factories developed by the current invention can produce D-lactic and/or L-acid lactic, allowing the synthesis of PDLA and/or PLLA in both eukaryotic and prokaryotic cells.

The subject of the present invention is therefore a method of producing PLLA or PDLA in a cell characterized by a carbon flux directed towards the synthesis of PDLA and/or PLLA.

PDLA synthesis includes the following steps:
i) conversion of pyruvate to D-lactate in an eukaryotic engineered cell
ii) synthesis of D-lactyl-CoA by thioesterification of D-lactate with a CoA donor, preferably acetyl-CoA;
iii) polymerization of D-lactyl-CoA molecules to PDLA.

PLLA synthesis includes the following steps:
i) conversion of pyruvate to L-lactate in a prokaryotic or an eukaryotic engineered cell.
ii) synthesis of L-lactyl-CoA by thioesterification of L-lactate with a CoA donor, preferably acetyl-CoA;
iii) polymerization of L-lactyl-CoA molecules to PLLA.

The cells express genes encoding for enzymes aimed at directing the carbon flux towards the synthesis of PDLA and/or PLLA.

In a preferred embodiment, the aforementioned cell is a eukaryotic cell, preferably a yeast cell, more preferably a *Saccharomyces* cell and even more preferably a *Saccharomyces cerevisiae* cell.

The yeasts are by way of example described in "The Yeasts" by N. J. W. Kreger-van Rij, 1987. In particular, the genus of yeast can be *Saccharomyces, Zygosaccharomyces, Candida, Hansenula, Kluyveromyces, Debaromyces, Nadsonia, Lipomyces, Torulopsis, Kloeckera, Pichia, Schizosaccharomyces, Trigonopsis, Brettanomyces, Cryptococcus, Trichosporon, Aureobasidium, Lipomyces, Phaffia, Rhodotorula, Yarrowia*, or *Schwanniomyces*, among others. Preferably, the yeast is selected from the genus *Saccharomyces*, and preferably is *Saccharomyces cerevisiae*. Preferably, the strains of *S. cerevisiae* are BY4742 (EuroScarf Accession No. Y10000), CEN.PK 102-5B (MATa, ura3-52, his3-11, leu2-3/112, TRP1, MAL2-8c, SUC2) and 113-11C (MATa, ura3-52, his3-11, TRP1, MAL2-8c, SUC2—Dr. P. Kötter, Institute of Microbiology, Johann Wolfgang Goethe-University, Frankfurt, Germany) or further from industrial strains such as AP, BL, SAU (Arome Plus, Blanche, Sauvignone available from AEB group, Italy) e VIN13 (available from Anchor, France). Yeast strains can be haploid or diploid.

The coordinated and appropriately regulated expression of the genes coding for the enzymes involved in the new metabolic pathway, introduced by the inventors of the present invention, can be achieved by using a strong and constitutive endogenous promoter, or by introducing more copies of the exogenous genes, or by means of the conversion of the nucleotide sequence with an optimized nucleotide variant in the codons. These are anyhow routine techniques under the competences of the experts in the field.

In one embodiment of the invention, the eukaryotic cell is able to produce PDLA by expressing exogenous genes, introduced therein, encoding the enzymes involved in polymer synthesis. In a preferred embodiment, the enzymes involved in the aforementioned PDLA production are: i) the enzyme D-lactate dehydrogenase (EC 1.1.1.28), ii) the enzyme propionyl-CoA transferase (EC 2.8.3.1), iii) the enzyme polyhydroxyalkanoate synthase (EC 2.3.1.B3). Any D-lactate dehydrogenase enzyme, propionyl-CoA transferase enzyme and polyhydroxyalkanoate synthase enzyme, whether encoded by an endogenous or heterologous gene, can be used according to the method of this invention. In a preferred embodiment, the heterologous gene encoding the enzyme D-lactate dehydrogenase is a mutated form of *E. coli* ldhA (Gene ID: 946315 NC 000913.3). Specifically, this sequence has the following nucleotide mutations: T387C, A537G, T636C, A663T, A726G, G777A, A798G, G825A, C828T, C885T (SEQ ID NO: 1).

In another preferred embodiment, the enzyme propionyl-CoA transferase is the mutated version of the enzyme propionyl-CoA transferase (Pct) of *Clostridium propionicum*. This mutated version, called Pct540, has an amino acid substitution at position 193 in which the valine is replaced by an alanine (V193A) (Park et al., WO2009/022797; Yang et al., 2010). Preferably, the "codon usage" of the heterologous gene encoding the Pct of *Clostridium propionicum* (Gene ID: AJ276553), mutated in the Pct540 version, is optimized for translation in yeast (SEQ ID NO: 2).

In a further preferred embodiment, the enzyme polyhydroxyalkanoate synthase is the mutated version of the enzyme polyhydroxyalkanoate synthase C1 (PhaC1) of *Pseudomonas resinovorans*. This mutated version, called PhaC1437Pre, has four amino acid substitutions, in which the glutamic acid at position 130 is replaced by aspartic acid (E130D), the serine at position 325 is replaced by threonine (S325T), the serine at position 477 is replaced from glycine (S477G), glutamine at position 481 is replaced by lysine (Q481K) (Yang et al., 2011). Preferably, the "codon usage" of the heterologous gene encoding the PhaC1 of *Pseudomonas resinovorans* (Gene Accession no.: AF129396), mutated in the PhaC1437Pre version, is optimized for translation in yeast (SEQ ID NO: 3).

In another embodiment of the invention, the cell is capable of producing PLLA by expressing exogenous genes, introduced therein, coding for the enzymes involved in the polymer synthesis. The enzymes involved in the aforementioned production are: i) the enzyme L-lactate dehydrogenase (EC 1.1.1.27), ii) the enzyme propionyl-CoA transferase (EC 2.8.3.1), iii) the enzyme polyhydroxyalkanoate synthase (EC 2.3.1.B3). Any L-lactate dehydrogenase enzyme, proprionyl-CoA transferase enzyme and polyhydroxyalkanoate synthase enzyme, whether encoded by an endogenous or heterologous gene, can be used according to the method of the invention. In a preferred embodiment, the heterologous gene encoding the enzyme L-lactate dehydrogenase is a mutated version of the ldh1 gene of *Lactobacillus plantarum* (Gene Accession no.: X70926). Specifically, this sequence has the following nucleotide mutations: T1A, T48C, C160G, G255T, G905C (Branduardi et al., 2006) (SEQ ID NO: 4).

In another preferred embodiment, the enzyme propionyl-CoA transferase is the mutated version of the enzyme propionyl-CoA transferase (Pct) of *Clostridium propionicum*. This mutated version, called Pct540, has an amino acid substitution at position 193 in which the valine is replaced by an alanine (V193A) (Park et al., WO2009/022797; Yang et al., 2010). Preferably the "codon usage" of the heterologous gene encoding the Pct of *Clostridium propionicum* (Gene ID: AJ276553), mutated in the Pct540 version, is optimized for translation in yeast (SEQ ID NO: 2).

In a further preferred embodiment, the enzyme polyhydroxyalkanoate synthase is the mutated version of the enzyme polyhydroxyalkanoate synthase C1 (PhaC1) of *Pseudomonas resinovorans*. This mutated version, called PhaC1437Pre, has four amino acid substitutions, in which the glutamic acid at position 130 is replaced by aspartic acid (E130D), the serine at position 325 is replaced by threonine (S325T), the serine at position 477 is replaced by glycine (S477G), glutamine at position 481 is replaced by lysine (Q481K) (Yang et al., 2011). Preferably, the "codon usage" of the heterologous gene encoding the PhaC1 of *Pseudomonas resinovorans* (Gene Accession no.: AF129396), mutated in the PhaC1437Pre version, is optimized for translation in yeast (SEQ ID NO: 3).

Surprisingly, the propionyl-CoA transferase and polyhydroxyalkanoate synthase enzymatic activities involved in PLLA production are the same as those required for PDLA synthesis. Unexpectedly, the present invention discloses that the enzymes propionyl-CoA transferase (Pct) and polyhydroxyalkanoate synthase C1 (PhaC1) can efficiently accept substrates in their enantiomeric form L. In literature there are no evidences that the enzyme propionyl-CoA transferase (Pct) can accept "in vivo" a substrate in the enantiomeric form L. The only study reported in literature has been conducted "in vitro" by Schweiger and Buckel (1984) and it shows that, although enzyme catalysis can occur on both isoforms, the enzyme has a clear preference of substrate with respect to D-lactate compared to the corresponding L form.

Similarly, considering the polyhydroxyalkanoate synthase, in literature there are no examples of polymerization conducted by this enzyme on monomers in the enantiomeric form L, independently from the polyhydroxyalkanoate synthase considered (type I, II, III). This is clearly documented in BRENDA, one of the main database for known enzymes (See website at brenda-enzymes.org). Consistently, the published productions of homo- and co-polymer of lactate in cells refer in fact to the polymerization of lactate monomers exclusively in the D form (Dusseaux et al., WO2017/108577; Lee et al., U.S. Pat. No. 9,120,891; and Cho et al., WO2006/126796).

Therefore, it is surprising that the cell(s) of the present invention is capable of producing a polyester biopolymer consisting of lactate monomers in the enantiomeric form L. This is further surprising if we consider that no polyester biopolymer synthesized by a cell (natural or engineered for the purpose) is constituted by monomers in enantiomeric form L: a clear example are the other polymers sharing bioplastic properties like the polyhydroxyalkanoates (PHA), which possess monomeric units exclusively in the D form (Singh and Yakhmi, 2017).

Since lactic acid is a key intermediate for the production of PDLA and/or PLLA, the intracellular production of this acid from glucose and/or other sugars, by engineering the expression levels of known genes, leads to an increase in production of lactic acid and therefore of PDLA and/or PLLA. Known engineered pathways for the efficient use of glucose and/or pentose sugars (xylose, arabinose) can be exploited for the production of PDLA and/or PLLA from sugars, which derive from residual biomass and therefore they are not in competition with the agri-food chain.

Therefore, according to a further embodiment, the cell able to produce PLLA/PDLA comprises intracellular levels of sugars and/or catabolic intermediates, deriving from them, greater than a corresponding wild-type cell, by cloning at least one of genes coding for proteins responsible for the internalization and/or catabolism of sugars. According to a preferred embodiment, said sugars are selected from glucose and carbohydrates deriving from chemical and/or enzymatic hydrolysis (enzymes belonging to the superfamilies of laccases, hydrolases, cellulases and hemicellulases, see Kumar et al., 2009) of a residual biomass. Preferably, said carbohydrates are hexoses and pentoses, including glucose, mannose, galactose, xylose, arabinose, and mixtures thereof. Therefore, the polymers of interest can be produced in a process that includes the hydrolysis of residual biomasses by enzymatic and/or chemical-physical means, for example by means of steam explosion, which leads to a solution enriched in simple sugars.

In addition or alternatively, intracellular lactic acid levels can be increased by eliminating competitive pathways to its production. As an illustrative and non-limiting example, the genes coding for pyruvate decarboxylase enzymes can be deleted (i.e. PDC1 Gene ID: 850733, Sequence NC_001144.5; PDC5 Gene ID ID: 850825, Sequence NC_001144.5; PDC6 Gene ID: 852978, Sequence NC_001139.9) and/or alcohol dehydrogenases, which lead to the formation of ethanol (i.e. ADH1 Gene ID: 854068, Sequence NC_001147.6).

Thus, in a further aspect the invention provides a process for the production of PLLA or PDLA that includes the following steps:
(i) culture of a cell as described herein in a culture medium comprising a carbon source;
(ii) recovery of the cell mass containing the polymer;
and optionally
(iii) extraction of PLLA or PDLA from cells.

The cell used for the production of PLLA can be prokaryotic or eukaryotic. The cell used for the production of PDLA is eukaryotic. In a preferred embodiment, the eukaryotic cell is a yeast cell, more preferably a *Saccharomyces* cell and even more preferably a *Saccharomyces cerevisiae* cell. In a further preferred embodiment of the process for producing PDLA and/or PLLA according to the invention, aforementioned carbon source can be chosen among glucose and other sugars deriving from the hydrolysis of a residual biomass (i.e. hexose, pentose). Preferably, said sugars are hexose, preferably glucose, or pentose, preferably xylose and/or arabinose, and mixtures thereof.

In a further preferred embodiment of the PDLA and/or PLLA production process according to the invention, said carbon source can be present in an amount from 10 g/L to 1000 g/L, preferably being 20 g/L and 100 g/L.

In another preferred embodiment, the culture medium is not supplemented with lactic acid.

PDLA and/or PLLA extraction from cells can be performed using solvents. Alternatively, the cellular biomass containing the polymer can be used directly.

DESCRIPTION OF THE PREFERRED EMBODIMENTS

Definitions

The term "biomass" defines any substance of organic origin that can regenerate in times compatible with its consumption, destined for the production of bioenergy and/or biofuels and/or biomaterials. This contrasts with fossil biomasses, whose regeneration times exceed their consumption by several orders of magnitude.

"Residual biomass" means the biodegradable fraction of waste and/or residues of biological origin from agriculture (including vegetable and/or animal compounds) and/or from forestry and/or related industries, including fishing and/or aquaculture, mowing and pruning from public and private green areas, as well as the biodegradable part of industrial and/or urban waste.

The "production yield" is defined as the ratio between the quantity of product obtained and the quantity of substrate consumed.

The term "vector" indicates a DNA construct comprising a DNA sequence that is linked to a control sequence capable of leading to the expression of the aforementioned DNA in a suitable host. In this invention the typical plasmid vector used has: a) or an origin of replication which allows the effective replication of the plasmid so that in each cell of the selected host there are tens of copies of the plasmid vector, or a DNA sequence which allows the integration of the plasmid vector in a chromosome of each cell of the chosen host; b) a selection marker such that a cell correctly transformed with the plasmid vector can be selected; c) a DNA sequence comprising recognition sites for restriction enzymes in order to introduce exogenous DNA into the plasmid vector by a process called ligation.

As generally reported in the state of the art, in order to express the gene inserted in the host cell, the coding sequence must be correctly and functionally related to regulatory elements of transcription, translation and expression functioning in the selected expression host.

The term "transformation" here used means that the DNA, once introduced into the cell, can replicate outside of chromosomes or as part of an entire chromosome.

EXAMPLES

Example 1: Construction of the recombinant vector pTEFLEU2-ldhA harboring the ldhA gene.

Figure 1:
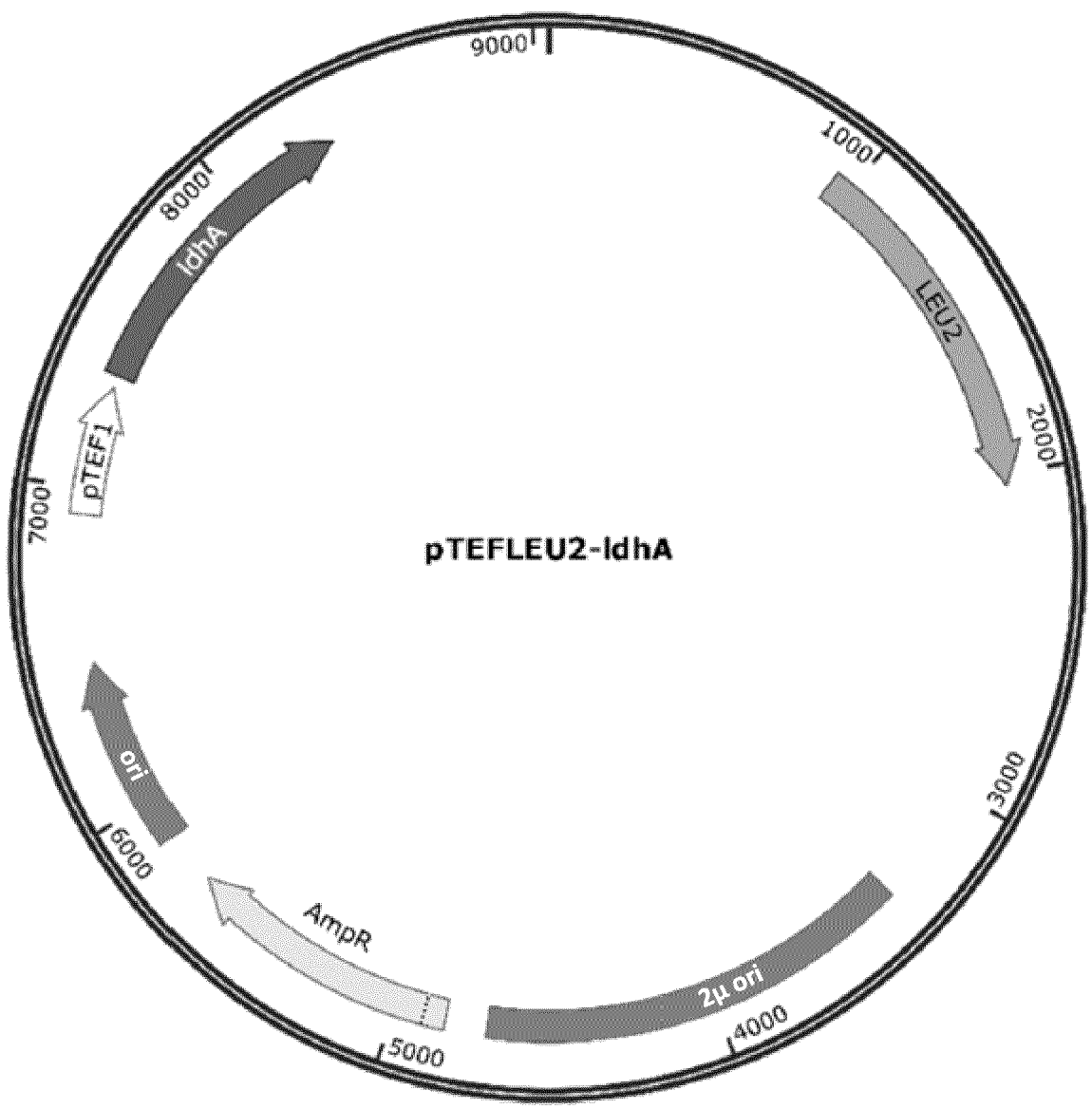
FIG. 1 shows the map of the recombinant vector pTE-FLEU2-ldhA harboring the ldhA gene deriving from *E. coli*.

The coding sequence of the ldhA gene was amplified by PCR using as a template the genomic DNA of *E. coli* and specific oligonucleotides (SEQ ID NO: 5; SEQ ID NO: 6). It is as follows: after 30 seconds of denaturation at 98° C., 25 cycles (denaturation of 10 seconds at 98° C., annealing of 30 seconds at 72° C. and elongation of 60 seconds at 72° C.), followed by a final elongation of 2 minutes at 72° C. The PCR product and the pTEFLEU2 target vector were digested with the EcoRI and XhoI restriction enzymes and after their ligation, the recombinant pTEFLEU2-ldhA vector was obtained (FIG. 1).

Example 2: Construction of the recombinant vector pTEFLEU2-ldh1 harboring the ldh1 gene.

Figure 2:
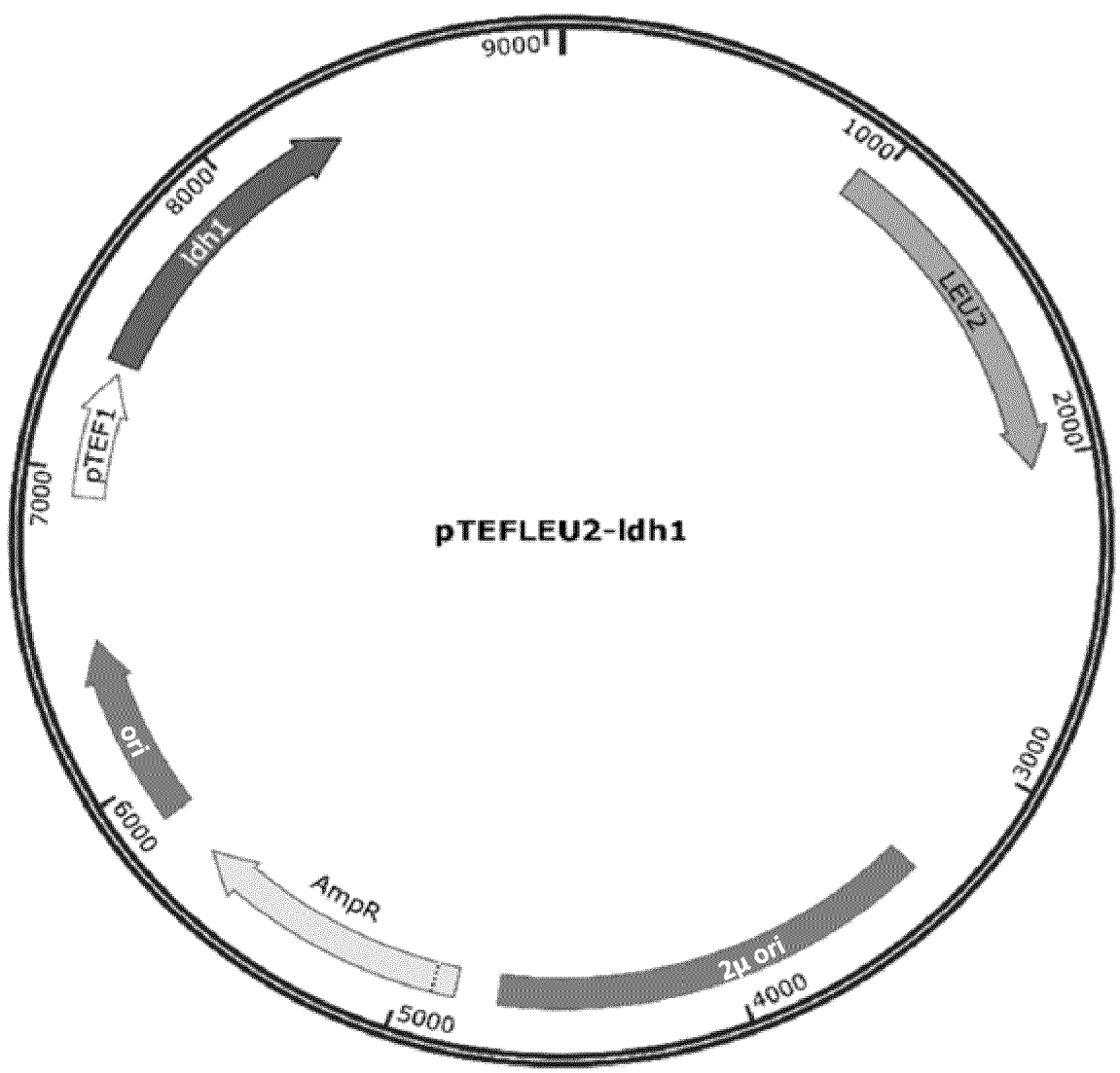
FIG. 2 shows the map of the recombinant vector pTE-FLEU2-ldh1 harboring the ldh1 gene deriving from *L. plantarum*.

The ldh1 gene of *L. plantarum* (SEQ ID NO: 4) was excised from the vector p022TLP (Branduardi et al., 2006) by digestion with the EcoRI restriction enzyme. The DNA fragment corresponding to the ldh1 gene having EcoRI ends was ligated with the target vector pTEFLEU2, after its digestion with EcoRI, leading to the obtainment of the recombinant expression vector pTEFLEU2-ldh1 (FIG. 2).

Example 3: Construction of the recombinant pYX212-Pct540 vector harboring the Pct540 gene.

Figure 3:
FIG. 3 shows the map of the recombinant vector pYX212-Pct540 harboring the Pct540 gene deriving from the Pct of *C. propiomicum*.

The coding sequence of the mutated version of the Pct gene of *C. propionicum*, Pct540 (SEQ ID NO: 3), preceded by the sequence of the pTDH3 promoter of *S. cerevisiae* (SEQ ID NO: 7) have been synthesized de novo and cloned by the manufacturing company into the pEX-A2 vector (Eurofins Genomics), obtaining the pEX-A2-Pct540 vector. In particular, the sequence of the Pct540 gene has codon usage optimized for yeast cells. The pEX-A2-Pct540 vector was linearized with the restriction enzyme BglI, and the pTDH3-Pct540 DNA fragment was excised from the aforementioned linearized vector, by digestion with the restriction enzymes KpnI and NheI. The pTDH3-Pct540 fragment with KpnI/NheI ends was cloned in the target vector pYX212 (R&D Systems, Inc., Wiesbaden, D), digested with the restriction enzymes KpnI and NheI and therefore lacking the pTPI promoter of *S. cerevisiae*. The ligation of the two DNA fragments led to the obtainment of the recombinant expression vector pYX212-Pct540 (FIG. 3).

Example 4: Construction of the recombinant vector pYX022-PhaC1437Pre harboring the PhaC1437Pre gene.

Figure 4:
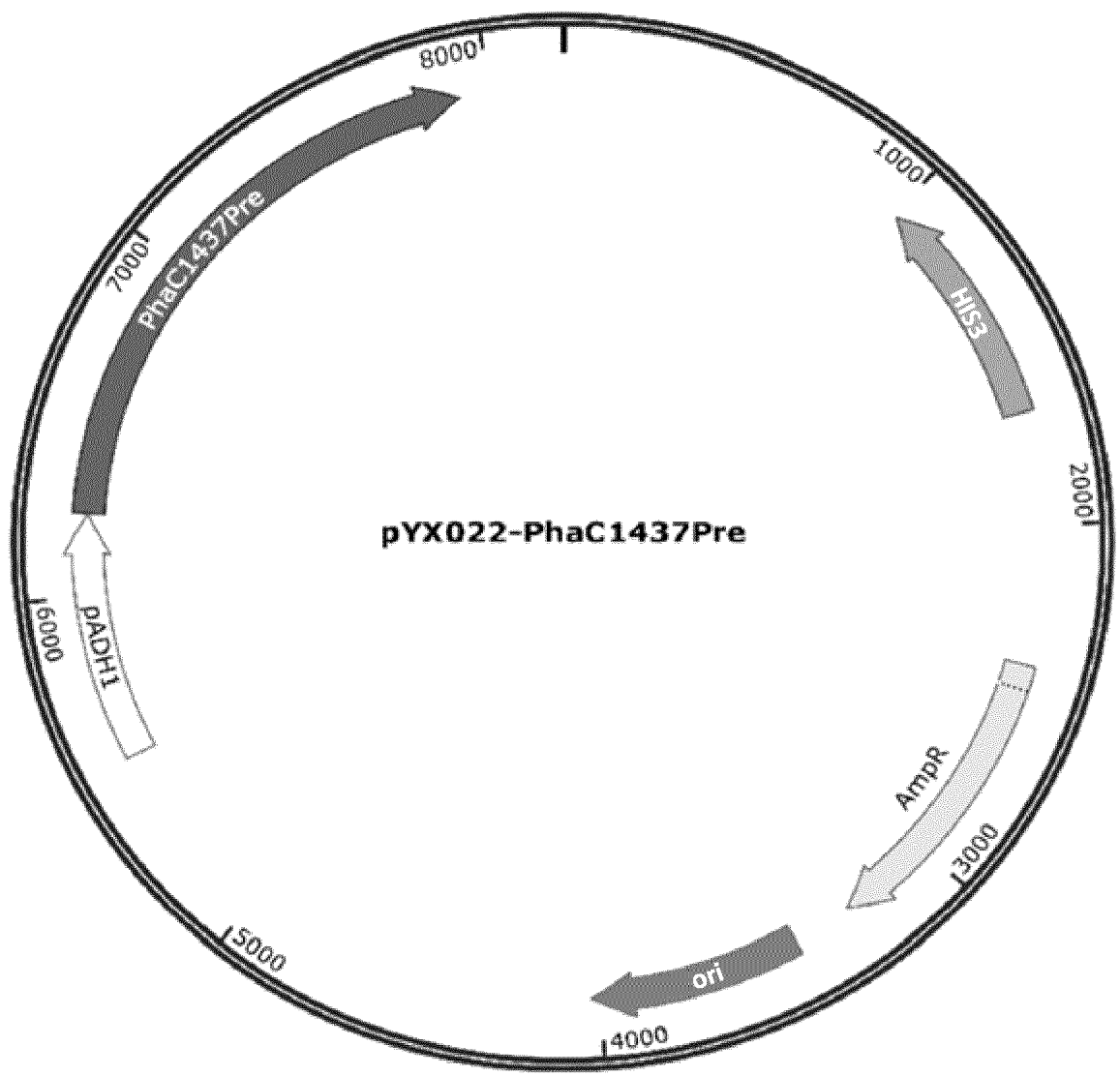
FIG. 4 shows the map of the recombinant vector pYX022-PhaC1437Pre harboring the PhaC1437Pre gene deriving from the PhaC1 of *P. resinovorans*.

The coding sequence of the mutated version of the PhaC1 gene of *P. resinovorans*, or PhaC1437Pre (SEQ ID NO: 3), preceded by the sequence of the pADH1 promoter of *S. cerevisiae* (SEQ ID NO: 8) have been synthesized de novo and cloned by the manufacturing company into the pEX-K4 vector (Eurofins Genomics). In particular, the PhaC1437Pre gene sequence has codon usage optimized for yeast cells. The pADH1-PhaC1437Pre DNA fragment was excised by the pEX-K4 vector by digestion with the restriction enzymes AatII and NheI. The pADH1-PhaC1437Pre fragment with AatII/NheI ends was cloned in the target vector pYX022 (R&D Systems, Inc., Wiesbaden, D), digested with the restriction enzymes AatII and NheI and therefore lacking the pTPI promoter of *S. cerevisiae*. The ligation of the two DNA fragments led to the obtainment of the recombinant expression vector pYX022-PhaC1437Pre (FIG. 4).

Example 5: Construction of the recombinant strain of *S. cerevisiae* for the production of PDLA.

Figure 5A:
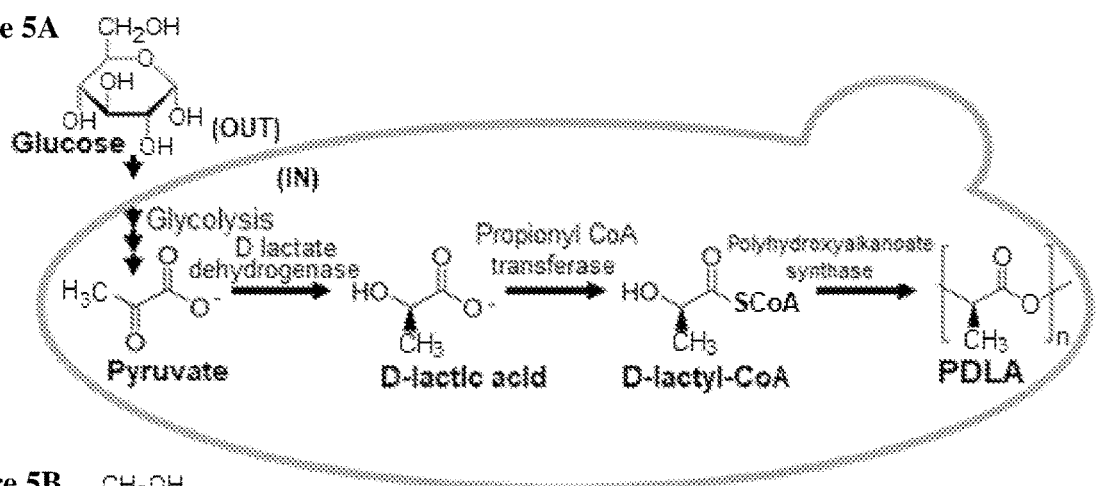
FIG. 5A shows the metabolic pathway for PDLA production starting from glucose via pyruvate, D-lactate and D-lactyl CoA.

The CEN.PK laboratory strain of *S. cerevisiae* was transformed with the vectors pTEFLEU2-ldhA, pYX212-Pct540 and pYX022-PhaC1437Pre, described respectively in examples 1, 3, 4. The graphic representation of the metabolic pathway for PDLA synthesis starting from glucose via pyruvate, D-lactate and D-lactoyl-CoA, in the recombinant strain is shown in FIG. 5A.

Example 6: Construction of the recombinant strain of *S. cerevisiae* for the production of PLLA.

Figure 5B:
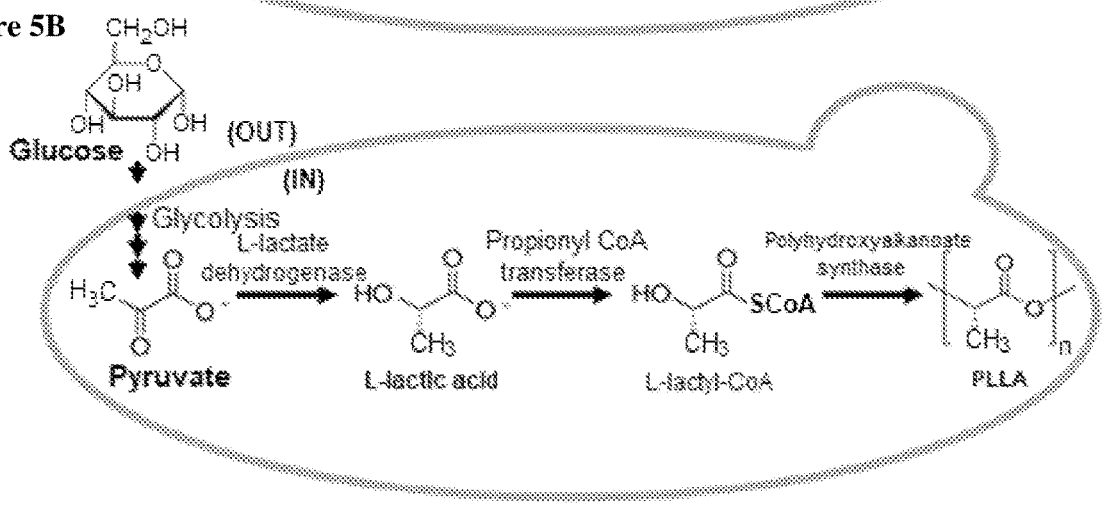
FIG. 5B shows the metabolic pathway for PLLA production from glucose via pyruvate, L-lactate and L-lactyl CoA.

The *S. cerevisiae* CEN.PK laboratory strain was transformed with the vectors pTEFLEU2-ldh1, pYX212-Pct540 and pYX022-PhaC1437Pre, described respectively in examples 2, 3, 4. The graphic representation of the metabolic pathway for PLLA synthesis starting from glucose via pyruvate, L-lactate and L-lactyl-CoA, in the recombinant strain is shown in FIG. 5B.

Example 7: Construction of the recombinant strain of *S. cerevisiae* as a negative control for PLA synthesis.

The *S. cerevisiae* CEN.PK laboratory strain was transformed with the pTEFLEU2-ldhA and pYX212-Pct540 vectors. The aforementioned recombinant strain lacks the polyhydroxyalkanoate synthase activity and it is therefore used in the following examples as a negative control for PDLA and PLLA production. In fact, independently of the stereochemistry of lactate, the absence of polyhydroxyalkanoate synthase activity does not allow the polymerization of lactyl-CoA monomers.

Example 8: Cell growth trend and production of the main extracellular metabolites over time in the engineered strain for PDLA production, in the engineered strain for PLLA production and in the control strain.

Cells of the CEN.PK pTEFLEU2-ldhA, pYX212-Pct540, pYX022-PhaC1437Pre strain engineered for the production of PDLA, of the CEN.PK pTEFLEU2-ldh1, pYX212-Pct540, pYX022-PhaC1437Pre strain engineered for the production of PLLA and CEN.PK pTEFLEU2-ldhA, pYX212-Pct540 strain (used as a control) were grown in the presence of glucose 20 g/L and Yeast Nitrogen Base (YNB) 6.7 g/L. The cells were inoculated at an optical density of 0.05 (OD 660 nm) in 20 mL of medium in 100 mL flasks and incubated at 30° C. on an orbital shaker at 160 rpm. Cell growth was monitored by measuring OD at 660 nm at regular time intervals. The extracellular concentration of glucose, acetate, ethanol and glycerol was determined by HPLC using $H_2SO_4$ 5 mN as a mobile phase and a Rezex ROA H+ column (8%) 300×7.8 mm with styrene sulfonate-divinylbenzene matrix (Phenomenex).

Figure 6:
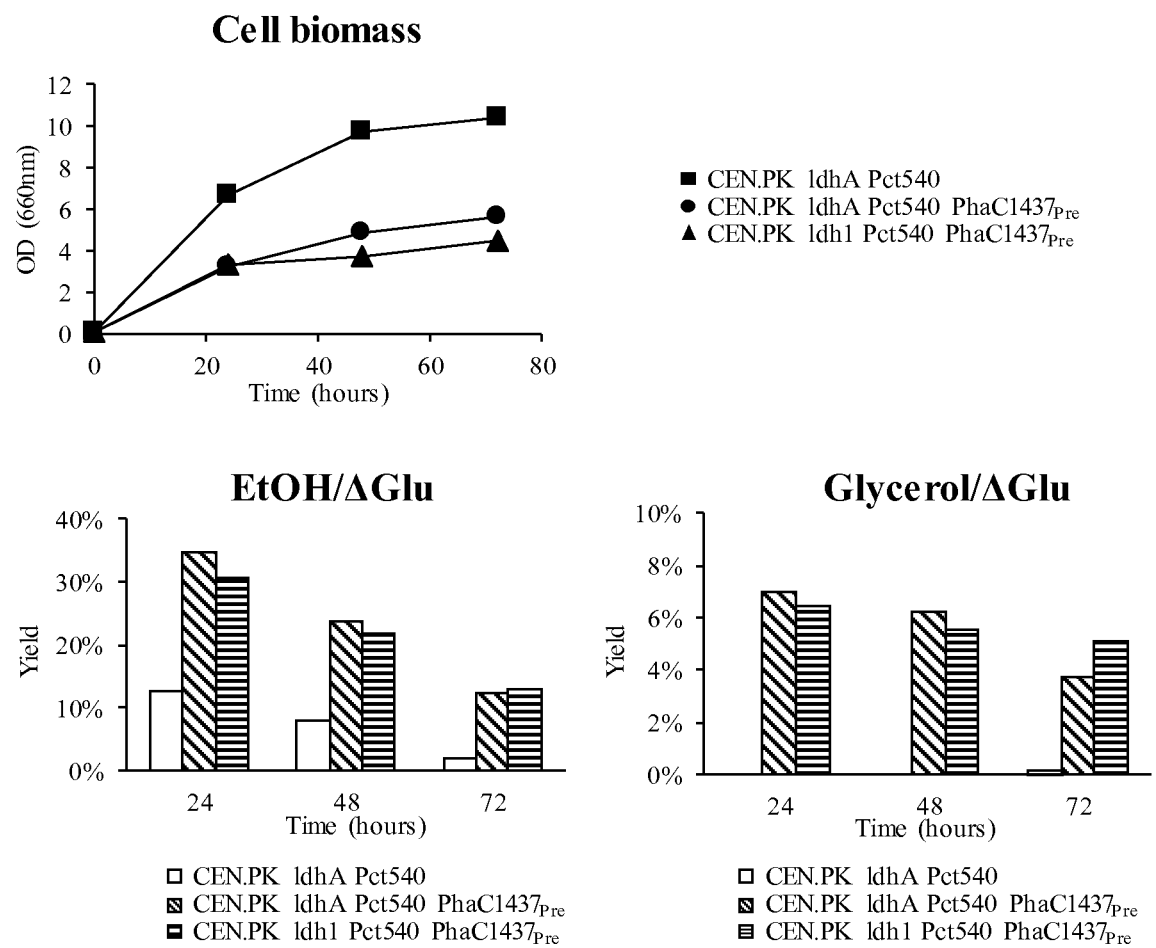
FIG. 6 shows a representative graph of the cell growth trend over time of an engineered strain for PDLA production, of an engineered strain for PLLA production and of a control strain expressing only the ldhA and Pct540 genes, providing glucose 20 g/L as carbon source (upper panel); histograms relating to the conversion yield of glucose into ethanol and of glucose into glycerol (lower panel)

As shown in FIG. 6 (upper panel) the CEN.PK strain engineered for PDLA production and the engineered strain for PLLA production strongly differ from the growth kinetic of the control strain. Surprisingly, these strains are characterized by a slower cell growth and by a lower cell biomass at the end of fermentation, compared to the CEN.PK pTEFLEU2-ldhA, pYX212-Pct540 strain, used as a control. Furthermore, also a comparative analysis of the growth kinetics of the strain producing PDLA or PLLA show some differences, even if less pronounced than the previous comparison. The results obtained are in accordance with the analysis of the main extracellular metabolites; the lower conversion yield of glucose into cell biomass of the engineered strains for the production of the two polymers corresponds in fact to higher conversion yields of glucose into ethanol and glycerol compared to the control strain CEN.PK pTEFLEU2-ldhA, pYX212-Pct540.

A carbon flux redirection in cells transformed with the genes encoding the enzymatic activities necessary for the production of PDLA and PLLA is demonstrated by these experiments.

Example 9: Evaluation of PDLA production or alternatively PLLA production by Nile red staining.

Figure 7:
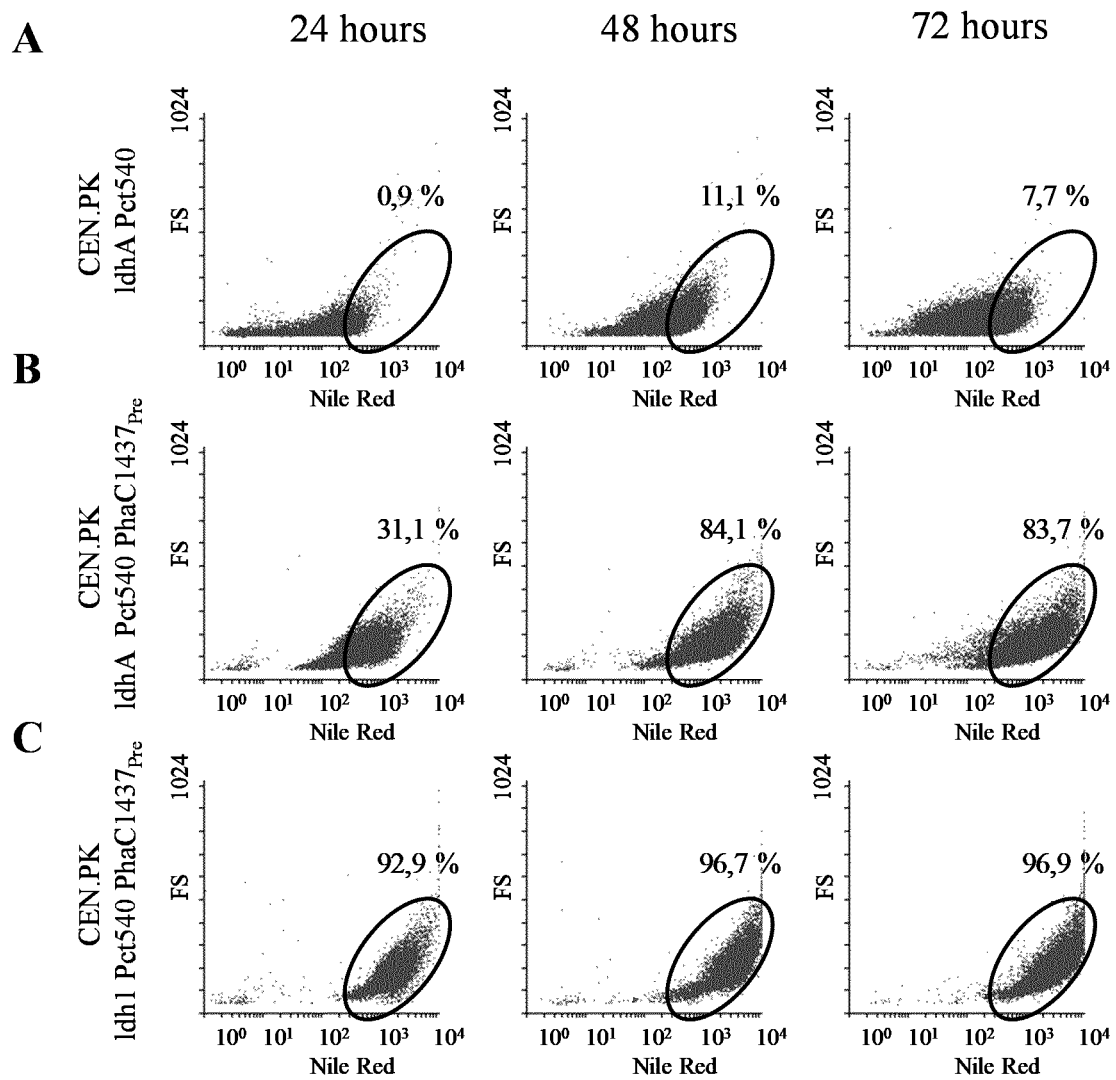
FIG. 7 shows the dot plots relating to the fluorescence emitted by cells stained with Nile red dye, for the control strain expressing ldhA and Pct540 (panel A), for the engineered strain for the production of PDLA (panel B) and for the engineered strain for PLLA production (panel C). These measurements were performed at different times from the inoculum (24 hours, 48 hours, 72 hours) by flow cytometry (FACS); in the graphs, the intensity of the fluorescence emitted at 620 nm is reported on a logarithmic scale on the abscissa axis while the Forward Scatter (FS) signal, relative to the cell size, is shown on the ordinate axis. The gate, fixed for all analyzes, indicates the percentage of cells positive to Nile red staining.

The cells of the CEN.PK strain engineered for PDLA production, of the engineered strain for PLLA production and of the control strain expressing only the ldha and Pct540 genes were grown as described in Example 8. The production of PDLA or alternatively of PLLA was evaluated by staining with Nile red dye. Nile red is generally used to evaluate in live cells the accumulation of aliphatic biopolymers, such as PHA or co-polymers of D-lactic acid and other hydroxy acids, as reported in literature, by way of example, by Spiekermann et al., 1999; Glorenflo et al., 1999; Yang et al., 2010. Specifically, after 24, 48 and 72 hours from the inoculum, 0.3 OD of cells of the strains were collected and after centrifugation washed with 1 mL of phosphate buffer (PBS; $NaH_2PO_4$ 53 mM, $Na_2HPO_4$ 613 mM, 75 mM NaCl). After centrifugation, they were resuspended in 1 mL of 35% (v/v) cold ethanol and incubated in ice for 20 minutes in order to permeabilize the cells to Nile red. The cells were washed again with 1 mL of PBS, and, after the addition of Nile red at the final concentration of 31.4 µM, they were incubated for 5 minutes in the dark in ice. Subsequently, the samples were analyzed by flow cytometry (FACS), using a Beckman Coulter FC-500 flow cytometer (Beckman Coulter, Fullerton, Calif., USA) equipped with an argon ion laser (excitation wavelength 488 nm, laser power 20 mW). The fluorescence emission of Nile red is acquired through a 670 nm filter (FL3 channel), in a logarithmic scale. The operating parameters were set to analyze 20 thousand cells for each sample excluding cellular debris. The data were subsequently analyzed using the Flowing software program (see website at flowingsoftware.com). FIG. 7 shows the dot plots related to the fluorescence emitted, at different times from the inoculum (24, 48, 72 hours), from cells stained with Nile red. Specifically, each dot represents a single cell; its position in the graph is dependent on its fluorescence emission (reported on the x-axis) and on its dimensions (shown on the y-axis).

The dot plots show that almost all the cells engineered for the production of PDLA (panel B) and for the production of PLLA (panel C) are positive to Nile red staining. In particular, the maximum percentage of cells positive to the staining is 84% in the engineered strain for PDLA production and 97% in the PLLA-engineered strain. On the contrary, as can be observed in panel A, in the control cells expressing only the ldhA and Pct540 genes, the percentage of staining positive cells is negligible and attributable to the interaction of Nile red with structural components of the cell, such as cell membranes (Mukherjee et al., 2007).

Given the direct correlation between the fluorescence emission of Nile red and the presence of aliphatic polymers, the reported data demonstrate that the metabolic engineering aimed at producing PDLA (FIG. 5A) and/or PLLA (FIG. 5B), object of the present invention, determine the accumulation of these polymers in eukaryotic cells.

Therefore, the synthesis of PDLA in eukaryotic cells by means of a one-step production, without the addition of lactate as substrate, without any mandatory need to attenuate or eliminate the ability to consume lactic acid as carbon source and without any mandatory need to increase the productivity of intracellular Coenzyme A (CoA) donor is described here for the first time. Furthermore, the direct synthesis of PLLA by cells is described for the first time. In literature no examples report wild-type or engineered cells capable of polymerizing hydroxy acids, and lactic acid among them, with a chiral center in L configuration. In particular, it has been described here for the first time that the enzyme polyhydroxyalkanoate synthase is able to polymerize hydroxy acid monomers with L configuration of the chiral center.

In addition, the cells of the CEN.PK strain engineered for PDLA production, of the engineered strain for PLLA production and of the control strain expressing only the ldha and Pct540 genes were grown on agar plates with molasses 20 g/L as carbon source, supplement with Nile red dye 0.5 µg/mL. After 4 days of incubation at 30° C., cell growth was observed in all the strains but only the strain engineered for PDLA production and that one engineered for PLLA production were able to accumulate intracellularly PDLA or PLLA, respectively, they indeed resulted stained with Nile red when exposed to UV light.

Example 10: Analysis of PDLA or alternatively of PLLA by GC-MS analysis.

In order to evaluate the composition of the polymer accumulated in the cells (example 9) a gas chromatography mass spectrometry (GC-MS) analysis was performed.

The cells of the engineered strain for PDLA production, of the engineered strain for PLLA production and of the control strain expressing only the ldha and Pct540 genes were pre-inoculated in the presence of glucose 50 g/L and YNB 6.7 g/L. The preinoculum was performed in 100 mL of medium in 500 mL flasks incubated at 30° C. on an orbital shaker at 160 rpm. After 24 hours of growth, cells were inoculated into a 2 L bioreactor at an initial OD660 of 0.2. The operating volume of the media used in the bioreactor is 1.5 L and its composition is: glucose 50 g/L and YNB 13.4 g/L.

Growth parameters are: constant temperature of 30° C.; amount of dissolved oxygen greater than 25% with an air flow of 1 vvm (volume of air per volume of culture medium); pH maintained at 5 with additions, if necessary, of NaOH 4M and H3PO4 at 25% (v/v). Agitation is dependent on the percentage of oxygen dissolved in the media.

After 48 hours from the inoculum, cells were collected by centrifugation and subjected to lyophilization and then to acid methanolysis in order to break the cells and depolymerize the lactic acid polymer into methyl lactate monomer units. Methanolysis was performed according to the following protocol adapted by Braunegg et al. (1978): the cells were dissolved in a solution of methanol acidified with sulfuric acid (3% v/v) and chloroform in a 1:1 ratio; the mixture was heated in microwave at a power of 300 W, for 200 minutes at 120° C. The solution resulting from the methanolysis of the cells was analyzed by GC-MS.

This instrument consists of a Clarus 500 gas chromatograph (PerkinElmer) and a Clarus 560 mass spectrometer (PerkinElmer). The GC is equipped with an Elite-5MS capillary column (PerkinElmer). The temperature conditions in which the gas chromatographic analysis was carried out are the following: 70° C. for 5 minutes, increase of 10° C./minute up to 150° C., increase of 20° C./minute to reach 300° C., maintained for 14.5 minutes. The sample was injected at an initial temperature of 250° C., maintained for 10 minutes.

Figure 8:
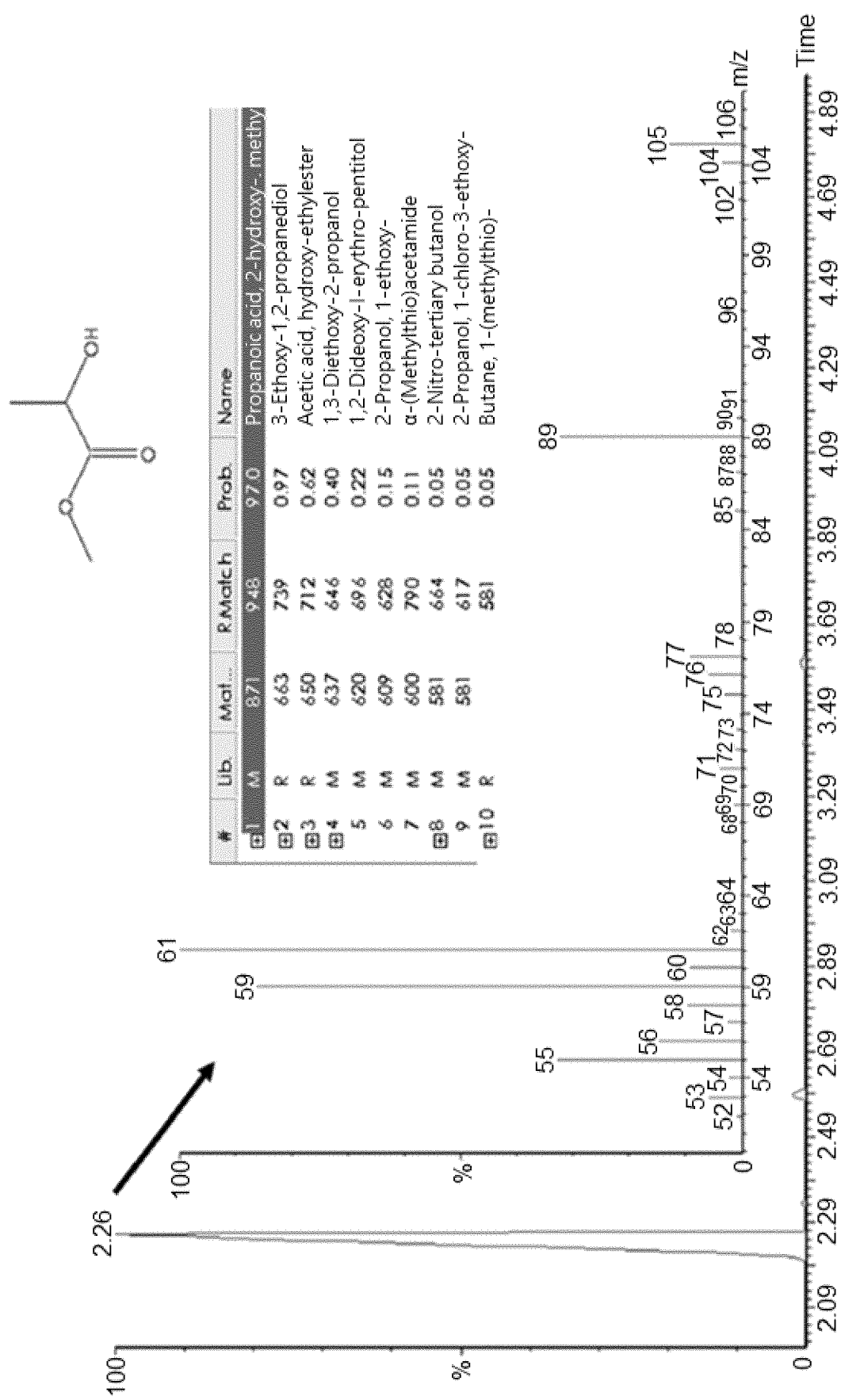
FIG. 8 shows the data relating to the GC-MS analysis of pure (commercial) lactic acid subjected to methanolysis in acidic conditions. The reported chromatogram is related to the first 5 minutes of analysis. For the single peak obtained, at the retention time of 2.26 minutes, the relative mass spectrum is reported with the percentage of identification with methyl lactate.

FIG. 8 shows the chromatogram and the mass spectrum related to a pure (commercial) lactate sample esterified to methyl lactate (according to the methanolysis protocol), used as reference for the subsequent analyses performed on the engineered cells to produce PDLA or alternatively PLLA. In the chromatogram only one peak is present, with a retention time of 2.26 minutes and, by comparison with the NIST Mass Spectral Library, it shows a 97% identification rate with methyl lactate.

Figure 9:
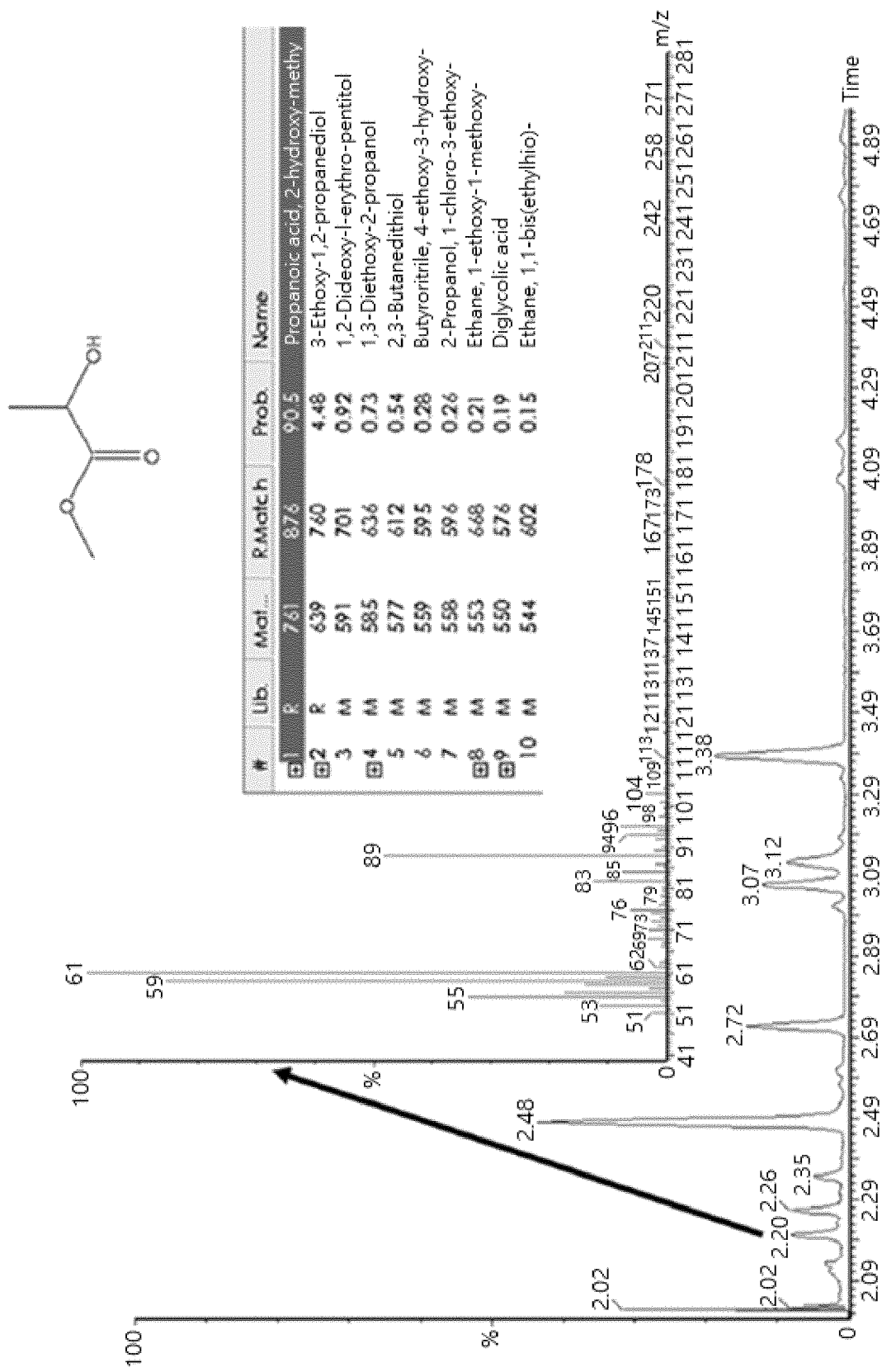
FIG. 9 shows data relating to the GC-MS analysis of cells engineered for PDLA production, lyophilized and subjected to methanolysis in acidic conditions. The reported chromatogram is related to the first 5 minutes of analysis. For the peak at the retention time of 2.20 minutes the relative mass spectrum is reported with the percentage of identification with methyl lactate.

FIG. 9 shows the GC-MS data relating to the engineered strain for PDLA production. The peak with a retention time of 2.20 minutes corresponds to methyl lactate, with a 90.5% identification with this molecule. This result shows that lactic acid is a constituent monomer of the biopolymer accumulated by the cells. The additional peaks present in the chromatogram are traceable to molecules released by the lysis of the cellular components.

Figure 10:
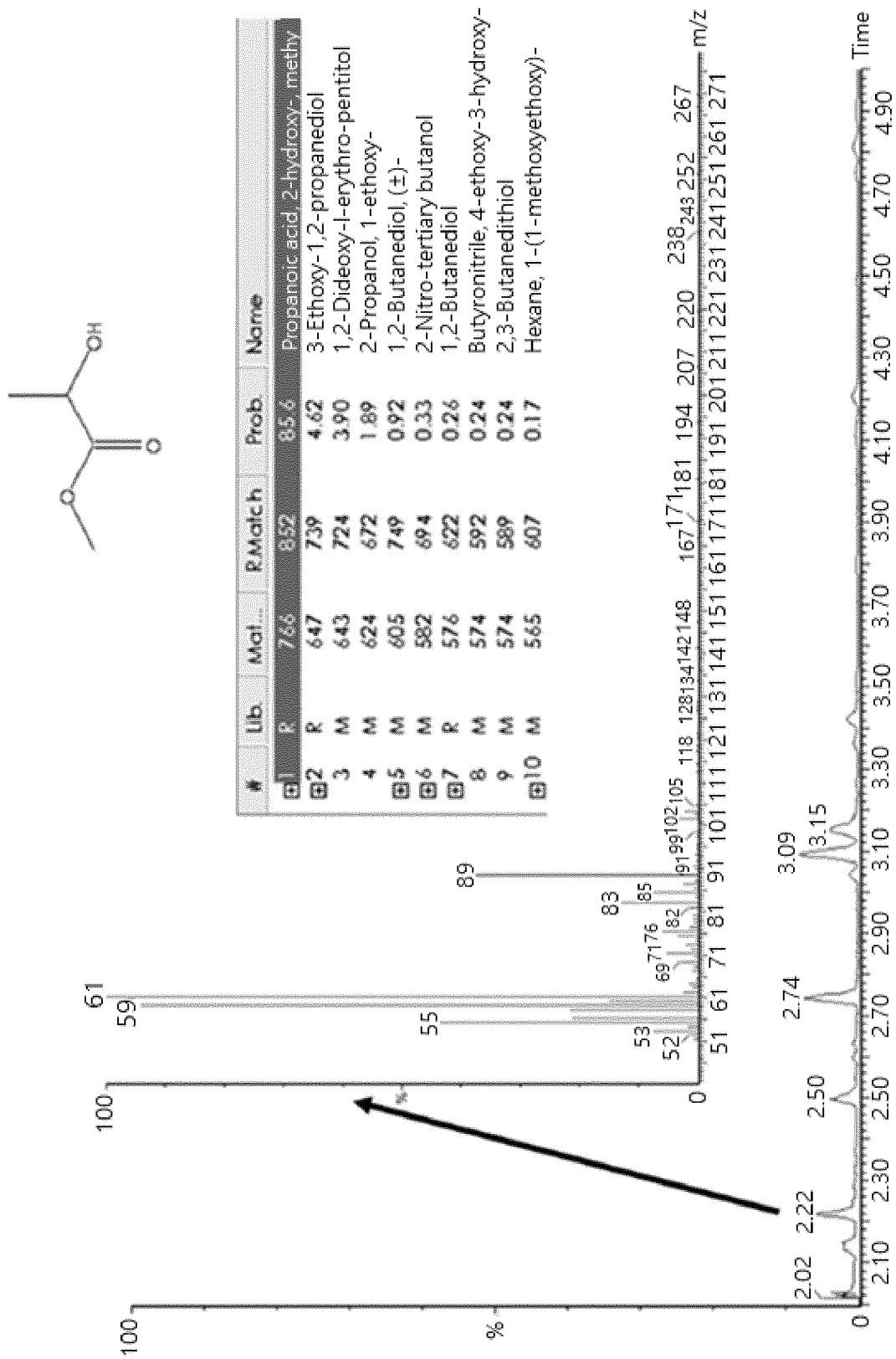
FIG. 10 shows the data relating to the GC-MS analysis of cells engineered for PLLA production, lyophilized and subjected to methanolysis in acidic conditions. The reported chromatogram is related to the first 5 minutes of analysis. For the peak at the retention time of 2.22 minutes the relative mass spectrum is reported with the percentage of identification with methyl lactate.

FIG. 10 shows the GC-MS data relating to the engineered strain for PLLA production. The peak with a retention time of 2.22 minutes corresponds to methyl lactate, with an 85.6% identification with this molecule. This result shows that lactic acid is a constituent monomer of the biopolymer accumulated by the cells. The additional peaks present in the chromatogram are also in this case traceable to molecules released by the lysis of the cellular components.

Figure 11:
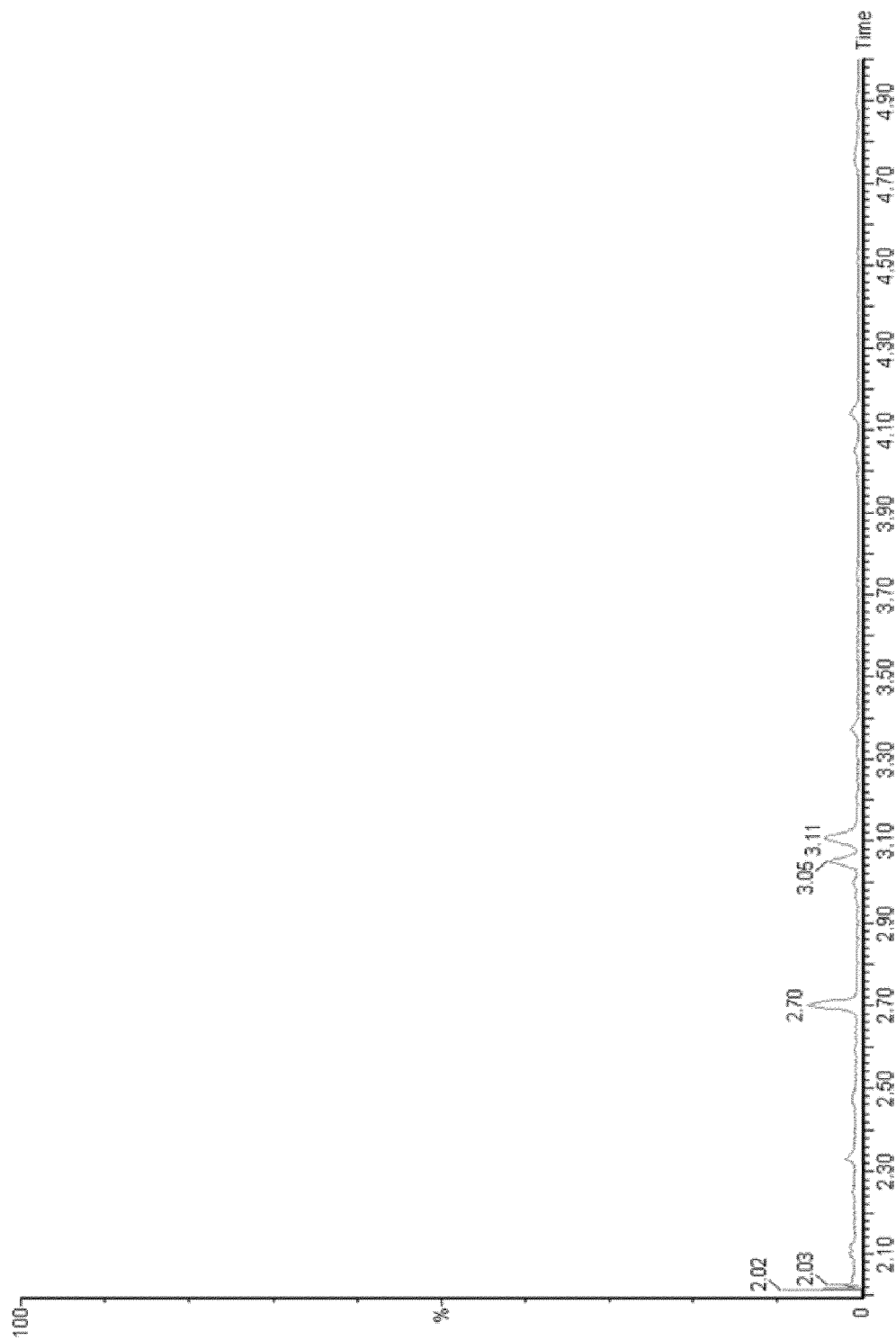
FIG. 11 shows the chromatogram relating to the first 5 minutes of GC analysis of lyophilized cells expressing ldhA and Pct and subjected to methanolysis.

FIG. 11 shows data relating to the control strain, expressing only the ldhA and Pct540 genes. The chromatogram shows peaks traceable to molecules released by cell lysis but not the one related to methyl lactate characterized by a retention time of about 2.2 minutes. This data therefore demonstrates that the peak relative to methyl lactate, identified in FIGS. 9 and 10, actually derives from the depolymerization of PDLA or alternatively of PLLA accumulated in specifically engineered cells, and not by free lactic acid in the cell.

Figure 12:
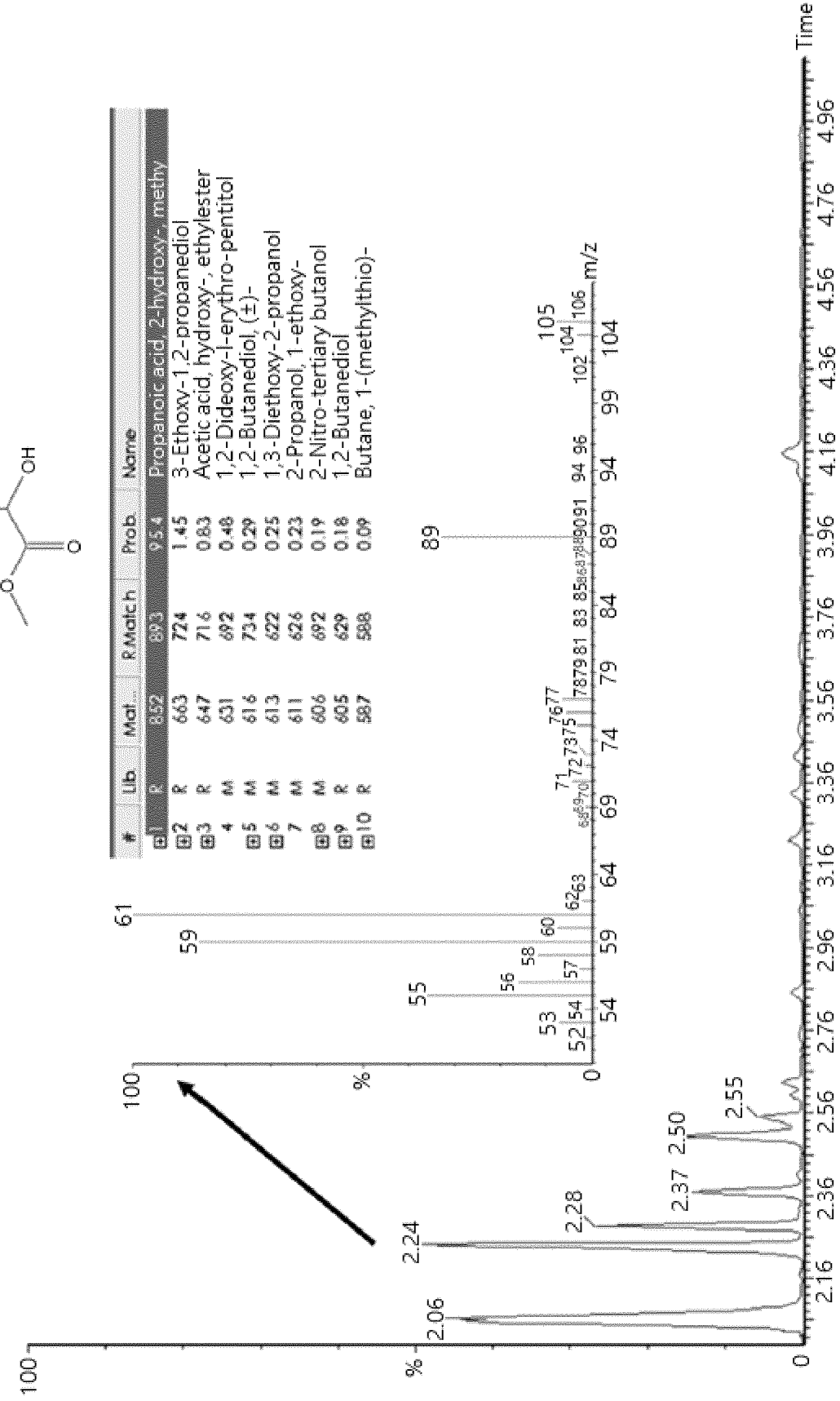
FIG. 12 shows the data relating to the GC-MS analysis of samples deriving from solvent extraction of lyophilized cells engineered for PDLA production and subjected to methanolysis in acidic conditions. The reported chromatogram is related to the first 5 minutes of analysis. For the peak at the retention time of 2.24 minutes the relative mass spectrum is reported with the percentage of identification with methyl lactate.

FIG. 12 shows the data relating to the GC-MS analysis of samples subjected to methanolysis in acidic conditions deriving from solvent extraction of lyophilized cells engineered for PDLA production. The extraction was carried out before the above-mentioned procedure of methanolysis in acid conditions, using chloroform and the Soxhlet apparatus (or extractor), as described by way of example, but not exclusive, by Yang et al. (2010), with minimal modifications. The peak with a retention time of 2.24 minutes corresponds to methyl lactate, with a 95.4% identification with this molecule. This result demonstrates that even after extraction with the Soxhlet apparatus it is possible to identify lactic acid as a constituent monomer of the biopolymer accumulated by the cells.

BIBLIOGRAPHY

Branduardi P, Sauer M, De Gioia L, Zampella G, Valli M, Mattanovich D, Porro D. Lactate production yield from engineered yeasts is dependent from the host background, the lactate dehydrogenase source and the lactate export. Microbial cell factories, 2006; 5(1):4.

Braunegg G, Sonnleitner B Y, Lafferty R M A rapid gas chromatographic method for the determination of poly-β-hydroxybutyric acid in microbial biomass. European journal of applied microbiology and biotechnology, 1978; 6(1):29-37.

Castaño-Cerezo S, Pastor J M, Renilla S, Bernal V, Iborra J L, Cánovas M. An insight into the role of phosphotransacetylase (pta) and the acetate/acetyl-CoA node in *Escherichia coli*. Microbial Cell Factories, 2009; 8:54.

Chen C Q and Patel M K. Plastics derived from biological sources: present and future: a technical and environmental review. Chemical reviews, 2011; 112(4): 2082-2099.

Cho J H, Park S J, Lee S Y, Jung Y K. Cells or plants having a producing ability of polylactate or its copolymers and method for preparing polylactate or its copolymers using the same. WO2006/126796

Choi M H, Ji G E, Koh K H, Ryu Y W, Park Y H. Use of waste Chinese cabbage as a substrate for yeast biomass production. Bioresource technology, 2002; 83(3), 251-253.

Choi S Y, Park S J, Kim W J, Yang J E, Lee H, Shin J, Lee S Y. One-step fermentative production of poly (lactate-co-glycolate) from carbohydrates in *Escherichia coli*. Nature biotechnology, 2016; 34(4):435.

Dusseaux S, Lajus S, Borsenberger V, Verbeke J, Bordes F, Marty A, Nicaud J M, Beopoulos A. WO2017/108577.

Garlotta D. A literature review of poly (lactic acid). Journal of Polymers and the Environment, 2001; 9(2):63-84.

Goldberg J S. PDLA a potential new potent topical analgesic: a case report. Local and regional anesthesia, 2014; 7, 59.

Gorenflo V, SteinbUchel A, Marose S, Rieseberg M, Scheper T. Quantification of bacterial polyhydroxyalkanoic acids by Nile red staining. Applied microbiology and biotechnology, 1999; 51(6), 765-772.

Jamshidian M, Tehrany E A, Imran M, Jacquot M, Desobry S. Poly-Lactic Acid: production, applications, nanocomposites, and release studies. Comprehensive Reviews in Food Science and Food Safety, 2010; 9(5): 552-571.

Jansen M L, Bracher J M, Papapetridis I, Verhoeven M D, de Bruijn H, de Waal P P, van Maris A J A, Klaassen P, Pronk J T. *Saccharomyces cerevisiae* strains for second-generation ethanol production: from academic exploration to industrial implementation. FEMS yeast research, 2017; 17(5).

Jung Y K, Kim T Y, Park S J, Lee S Y. Metabolic engineering of *Escherichia coli* for the production of polylactic acid and its copolymers. Biotechnology and bioengineering, 2010; 105(1):161-171.

Kumar P, Barrett D M, Delwiche M J, Stroeve P. Methods for Pretreatment of Lignocellulosic Biomass for Efficient Hydrolysis and Biofuel Production. Industrial & Engineering Chemistry Research, 2009; 48(8):3713-3729.

Lee S Y, Jung Y K, Yang T H, Park S J, Kim T W, U.S. Pat. No. 9,120,891.

Li M e Borodina I. Application of synthetic biology for production of chemicals in yeast *Saccharomyces cerevisiae*. FEMS yeast research, 2015; 15(1), 1-12.

Maillard D, Prud'homme RE. Differences between crystals obtained in PLLA-rich or PDLA-rich stereocomplex mixtures. Macromolecules, 2010; 43(9), 4006-4010.

Marco M B, Moineau S, Quiberoni A. Bacteriophages and dairy fermentations. Bacteriophage, 2012; 2(3):149-158.

Mathuriya A S and Yakhmi J V. Polyhydroxyalkanoates: Biodegradable Plastics and Their Applications. Handbook of Ecomaterials, 2017; 1-29.

Mukherjee S, Raghuraman H, Chattopadhyay A. Membrane localization and dynamics of Nile Red: effect of cholesterol. Biochimica et Biophysica Acta (BBA)-Biomembranes, 2007; 1768(1), 59-66.

Okano K, Tanaka T, Ogino C, Fukuda H, Kondo A. Biotechnological production of enantiomeric pure lactic acid from renewable resources: recent achievements, perspectives, and limits. Appl Microbiol Biotechnol., 2010; 85:413-423.

Park S J, Yang T H, Kang H O, Lee S H, Lee E J, Kim T W. Mutant of propionyl-coa transferase from *Clostridium propionicum* and preparing method for PLA or PLA copolymer using the same, WO2009/022797.

Porro D, Gasser B, Fossati T, Maurer M, Branduardi P, Sauer M, Mattanovich D. Production of recombinant proteins and metabolites in yeasts. Applied microbiology and biotechnology, 2011; 89(4):939-948.

Rasal R M, Janorkar A V, Hirt D E. Poly (lactic acid) modifications. Progress in polymer science, 2010; 35(3): 338-356.

Schweiger G and Buckel W. On the dehydration of (R)-lactate in the fermentation of alanine to propionate by *Clostridium propionicum*. FEBS letters, 1984; 171(1), 79-84.

Soares J, Demeke M M, Van de Velde M, Foulquie-Moreno M R, Kerstens D, Sels B F, Verplaetse A, Ribeiro Fernandes A A, Thevelein J M, Fernandes P M B. Fed-batch production of green coconut hydrolysates for high-gravity second-generation bioethanol fermentation with cellulosic yeast. Bioresource technology, 2017; 244: 234-242.

Spiekermann P, Rehm B H, Kalscheuer R, Baumeister D, Steinbüchel A. A sensitive, viable-colony staining method using Nile red for direct screening of bacteria that accumulate polyhydroxyalkanoic acids and other lipid storage compoundfiguis. Archives of microbiology, 1999; 171(2), 73-80.

Tsuji H, Auras R, Lim L-T, Selke S E M. Poly (lactic acid): synthesis, structures, properties, processing, and applications. Wiley, 2011.

Xiao L, Wang B, Yang G, Gauthier M. Poly (lactic acid)-based biomaterials: synthesis, modification and applications. In Biomedical science, engineering and technology. InTech, 2012.

Yang T H, Jung Y K, Kang H O, Kim T W, Park S J, Lee S Y. Tailor-made type II *Pseudomonas* PHA synthases and their use for the biosynthesis of polylactic acid and its copolymer in recombinant *Escherichia coli*. Applied microbiology and biotechnology, 2011; 90(2):603-614.

Yang T H, Kim T W, Kang H O, Lee S H, Lee E J, Lim S C, Oh S O, Song A J, Park S J, Lee S Y. Biosynthesis of polylactic acid and its copolymers using evolved propionate CoA transferase and PHA synthase. Biotechnology and bioengineering, 2010; 105(1):150-160.

SITOGRAPHY website appearing at european-bioplastics.org
appearing at brenda-enzymes.org
website appearing at flowingsoftware.com

---

The invention claimed is:

1. A cell able to produce poly-L-lactic acid (PLLA), wherein said cell comprises:
   (i) a L-lactate dehydrogenase enzyme encoded by the *Lactobacillus plantarum* L-lactate dehydrogenase ldh 1 gene having the nucleotide sequence of SEQ ID NO:4, wherein said L-lactate dehydrogenase enzyme catalyzes the conversion of pyruvate into L-lactate;
   (ii) an acyl-CoA transferase enzyme which is a propionyl-CoA transferase enzyme encoded by a gene having the nucleotide sequence of SEQ ID NO:2, wherein said gene is a mutated form of the *Clostridium propionicum* propionyl-CoA transferase gene, and wherein said acyl-CoA transferase enzyme catalyzes the synthesis of L-lactoyl-CoA by thioesterification of L-lactate; and
   (iii) a polyhydroxyalkanoate synthase enzyme encoded by a gene having the nucleotide sequence of SEQ ID NO:3, wherein said gene is a mutated form of the *Pseudomonas resinovorans* polyhydroxyalkanoate synthase C1 gene, and wherein said polyhydroxyalkanoate synthase enzyme catalyzes the polymerization of L-lactoyl-CoA into PLLA;
   wherein said cell able to produce PLLA is a yeast cell.

2. The cell according to claim 1, wherein said yeast is *Saccharomyces cerevisiae*.

3. The cell according to claim 1, further containing one or more genes responsible for sugar internalization and/or catabolism.

4. The cell according to claim 1, wherein the genes encoding the pyruvate decarboxylase and/or alcohol dehydrogenase enzymes, involved in ethanol formation, are partially or completely deleted.

5. The cell according to claim 1, further containing one or more genes responsible for sugar internalization and/or catabolism.

6. The cell according to claim 1, further containing one or more genes responsible for sugar internalization and/or catabolism.

7. A method for producing poly-L-lactic acid (PLLA), which comprises the following steps:
   (i) cultivating the cell according to claim 1 in a culture medium containing a carbon source;
   (ii) recovering the cell mass containing the polymer; and
   (iii) extracting PLLA from the cells.

8. The method according to claim 7, wherein said carbon source is selected from hexose sugar monomers; pentose sugar monomers; and disaccharides.

9. The method according to claim 7, wherein the culture medium is not supplemented with lactic acid.

10. A method for producing poly-L-lactic acid (PLLA), which comprises the following steps:
  (i) cultivating the cell according to claim 1 in a culture medium containing a carbon source; and
  (ii) recovering the cell mass containing the polymer.

11. The method of claim 8, wherein the hexose and/or pentose sugar monomers are selected from the group consisting of glucose, fructose, galactose, mannose, xylose, and arabinose, and wherein the disaccharides are selected from the group consisting of lactose and saccharose.

12. The method according to claim 8, wherein the culture medium is not supplemented with lactic acid.

* * * * *

SEQUENCE LISTING

```
<160> NUMBER OF SEQ ID NOS: 8

<210> SEQ ID NO 1
<211> LENGTH: 990
<212> TYPE: DNA
<213> ORGANISM: Escherichia coli

<400> SEQUENCE: 1
atgaaactcg ccgtttatag cacaaaacag tacgacaaga agtacctgca acaggtgaac     60
gagtcctttg gctttgagct ggaattttt  gactttctgc tgacggaaaa aaccgctaaa    120
actgccaatg gctgcgaagc ggtatgtatt ttcgtaaacg atgacggcag ccgcccggtg    180
ctggaagagc tgaaaaagca cggcgttaaa tatatcgccc tgcgctgtgc cggtttcaat    240
aacgtcgacc ttgacgcggc aaaagaactg gggctgaaag tagtccgtgt tccagcctat    300
gatccagagg ccgttgctga acacgccatc ggtatgatga tgacgctgaa ccgccgtatt    360
```

-continued

```
caccgcgcgt atcagcgtac ccgtgacgct aacttctctc tggaaggtct gaccggcttt      420
actatgtatg caaaacggc aggcgttatc ggtaccggta aaatcggtgt ggcgatgctg       480
cgcattctga aaggttttgg tatgcgtctg ctggcgttcg atccgtatcc aagtgcggcg      540
gcgctggaac tcggtgtgga gtatgtcgat ctgccaaccc tgttctctga atcagacgtt      600
atctctctgc actgcccgct gacaccggaa aactaccatc tgttgaacga agccgccttc      660
gatcagatga aaatggcgt gatgatcgtc aataccagtc gcggtgcatt gattgattct      720
caggcggcaa ttgaagcgct gaaaaatcag aaaattggtt cgttgggtat ggacgtatat     780
gagaacgaac gcgatctgtt ctttgaagat aaatccaacg acgtaattca ggatgacgta     840
ttccgtcgcc tgtctgcctg ccacaacgtg ctgtttaccg gcatcaggc attcctgaca      900 gcagaagctc tgaccagtat ttctcagact acgctgcaaa acttaagcaa tctggaaaaa     960
ggcgaaacct gcccgaacga actggtttaa                                       990
```

<210> SEQ ID NO 2
<211> LENGTH: 1575
<212> TYPE: DNA
<213> ORGANISM: Clostridium propionicum

<400> SEQUENCE: 2

```
atgagaaaag ttccgataat tactgctgac gaagctgcaa agttgatcaa agatggtgat       60
acagtaacca cttcgggttt tgtcggtaat gctattcctg aggcgttaga cagagccgtt      120
gaaaagagat tcttggaaac tggcgaacct aagaatatca cctatgtcta ttgtggtagc      180
caagggaaca gagatggaag gggtgcagaa catttttgccc atgaaggact actgaaaagg     240
tatattgcag acattgggc tacagttcca gcgttgggga aaatggctat ggaaaacaaa      300
atggaagcgt ataatgtctc tcaaggcgcc ttatgtcact tgtttaggga tatagcgagt     360
cacaaacctg gcgtctttac taaagtgggt attggcactt tcatagaccc tagaaatggc     420 ggtgaaaag tgaacgatat tacgaaagaa gatattgttg agcttgttga aatcaaaggg     480
caagaatact tgttctatcc tgcctttccc atacatgttg ccttgataag aggtacatat      540
gctgatgaat cagggaacat aactttcgag aaagaagccg ctccgttgga aggaacatct     600
gtatgtcaag ctgtaaagaa tagtggaggt attgtagttg tccaggtaga aagagtggta     660
aaggcaggga cattggatcc acgtcacgtt aaggttccag gaatttacgt tgattacgtt     720
gttgtggcag atcctgagga tcaccaacag tcattagatt gcgagtatga tcccgcactt     780
tctggtgaac atcgtagacc agaagttgtt ggtgagccat acctctttc cgccaagaaa      840 gtgataggca aagaggtgc tattgagctt gagaaggacg tggctgtaaa cttaggtgta     900
ggtgctccgg aatatgtcgc atcagtcgct gacgaagaag cattgtgga ttttatgacc     960 ttaactgcag aatctggcgc tattggaggc gttccagctg gtggagttag atttggtgca    1020
tcctataatg ccgatgcact aatcgatcaa ggataccagt tgactactta tgatggtggt   1080
ggtttagact tatgctactt gggactggcc gagtgtgacg agaaaggtaa cattaatgtt   1140
tcgcgttttg gtcccaggat tgcaggatgt ggaggtttca ttaatataac tcagaatacg   1200
ccaaaagtgt tcttttgtgg cacattcact gcaggcggt tgaaggtcaa atcgaggac     1260 ggtaaagtca tcatcgtaca agaagggaag caaaagaaat tcttaaggc tgtggaacag   1320 ataacattca atggcgacgt tgctttagcc aacaagcaac aagtaaccta cattacggaa   1380
agatgcgttt tcttactgaa ggaagatggt ctacatctat ccgaaattgc accaggtatt   1440
gacttgcaaa cccaaaatact agatgtcatg gactttgctc caatcatcga tagagatgcg   1500
```

```
aatggtcaga tcaaactgat ggatgccgct ttgtttgcag aagggttaat gggtttgaaa    1560
gagatgaaaa gctaa                                                     1575

<210> SEQ ID NO 3
<211> LENGTH: 1680
<212> TYPE: DNA
<213> ORGANISM: Pseudomonas resinovorans

<400> SEQUENCE: 3
atgtcaaaca agaacaacga agatttgcaa agacaagcaa gcgataacac cctgaatttg      60
aacccagtta ttggtataag aggcaaagac ctactgtcaa gcgctagaat ggtgctattg     120
caagctataa agcaacccct tcattctgcc aaacatgttg cgcactttgg attggagtta     180
aagaatgtct tgttggggca atcgggactt caaccagaag cagatgatag aagatttaac     240
gatccagctt ggtcacaaaa tcccttgtat aagcgttatc tacagacata cttggcttgg     300
agaaaggaat tacattcttg gatagatgaa tctaacttgt cctcacaaga cgcatctaga     360
ggtcacttcg ttataaactt gatgaccgat gctatggcac ctaccaattc catggctaac     420
cctgcagccg tcaagagatt ctttgagact ggtgggaaat ccttactaga tggattaagt     480
catctggcca agacatggt aaataatggt ggtatgcctt ctcaggtcaa tatggatgca     540
tttgaagttg gtcagaattt agcaactacc gagggagctg tagtgttcag aaacgatgtt     600
ttagagttga ttcaatacaa acccattacc gaatcagtgt atgaacgtcc gttacttgtt     660
gttccgcccc agattaacaa attttacgtg ttcgacttgt cacctgaaaa gtctttagcc     720
agattttgct tgaggagtaa tctgcaaaca ttcatcgtaa gttggagaaa tcctactaag     780
gctcagagag aatggggttt aagcacgtat attgaggcac taaaggaagc aattgacgtg     840
atattgaaaa tcacgggtgc aaaagatctg aatatcctag gtgcttgttc tggcggtatt     900
acgaccgtag cgttacttgg tcactatcag gctattggtg agacaaaagt caatgccttt     960
acacagatgg tcactgtctt agattttaac ttggatagtc aagtggccct atttgctgat    1020
gaacaaacgt tagaagctgc caaaaggaga tcataccaag ctggagtttt ggaagggaag    1080
gatatggcta agttttcgc ttggatgagg cctaacgatc tgatttggaa ttattgggtt    1140
aacaattact tacttggcaa tgaaccacca gcatttgaca tcttgtattg gaataatgac    1200
actactaggt taccagcagc ctttcatggt gagttagttg agatgttcaa gactaacgct    1260
cttactagac aaatgctctc tgaagtatgt ggcactccta tagacttgaa gcaagtaaca    1320
tcggatttct tttgtcttgc cggtacaaca gaccacatta ctccttggga agcctgttat    1380
cgtagcgcat tgctacttgg aggtaaatgc gagtttgtct tgtccaatgg aggccacatc    1440
aaatcgatct tgaatccacc agggaatcca aaagcaagat tctccacagg atccgaaatg    1500
cctaaagacc aaaagcgtgt gttagaaaac gctaccaaac atgcggattc ttggtggctg    1560
cattggcaac aatggattgg cgaaagaagt ggtaaaacta agaaagcgag tttcacatta    1620
ggcaataagg ccttttccagc gggtgaagct tctccgggta catacgttca tgaaaggtaa    1680

<210> SEQ ID NO 4
<211> LENGTH: 963
<212> TYPE: DNA
<213> ORGANISM: Lactobacillus plantarum
```

<400> SEQUENCE: 4

```
atgtcaagca tgccaaatca tcaaaaagtt gtgttagtcg gcgacggcgc tgttggttct      60
agttacgctt ttgccatggc acaacaagga attgctgaag aatttgtaat tgtcgatgtt     120
gttaaagatc ggacaaaggg tgacgccctt gatcttgaag acgcccaagc attcaccgct     180
cccaagaaga tttactcagg cgaatattca gattgtaagg acgctgactt agttgttatt     240
acagccggtg cgcctcaaaa gcctggtgaa tcacgtttag acttagttaa caagaattta     300
aatatcctat catccattgt caaaccagtt gttgactccg gctttgacgg catcttctta     360
gttgctgcta accctgttga catcttaact tacgctactt ggaaattctc aggttttcca     420
aaggatcgtg tcattggttc agggacttcc ttagactctt cacgtttacg cgttgcgtta     480
ggcaaacaat tcaatgttga tcctcgttcc gttgatgctc acatcatggg tgaacacggt     540
gattctgaat tgctgctta ctcaactgca accatcggga cacgtccagt tcgcgatgtc     600
gctaaggaac aaggcgtttc tgacgaagat ttagccaagt tagaagatgg tgttcgtaac     660
aaagcttacg acatcatcaa cttgaagggt gccacgttct acggtatcgg gactgcttta     720
atgcggattt ccaaagccat tttacgtgat gaaaatgccg ttttaccagt aggtgcctac     780
atggacggcc aatacggctt aaacgacatt tatatcggga ctccggctgt gattggtgga     840
actggtttga acaaatcat cgaatcacca ctttcagctg acgaactcaa gaagatgcaa     900
gattccgccg caactttgaa aaaagtgctt aacgacggtt agctgaatt agaaaataaa     960
taa                                                                    963
```

<210> SEQ ID NO 5
<211> LENGTH: 41
<212> TYPE: DNA
<213> ORGANISM: Artificial Sequence
<220> FEATURE:
<223> OTHER INFORMATION: primer FW ldha

<400> SEQUENCE: 5

```
cttagaattc atgaaactcg ccgtttatag cacaaaacag t                          41
```

<210> SEQ ID NO 6
<211> LENGTH: 37
<212> TYPE: DNA
<213> ORGANISM: Artificial Sequence
<220> FEATURE:
<223> OTHER INFORMATION: primer REV ldha

<400> SEQUENCE: 6

```
tgtactcgag ttaaaccagt tcgttcgggc aggtttc                               37
```

<210> SEQ ID NO 7
<211> LENGTH: 667
<212> TYPE: DNA
<213> ORGANISM: Saccharomyces cerevisiae

<400> SEQUENCE: 7

```
tcattatcaa tactgccatt tcaaagaata cgtaaataat taatagtagt gattttccta      60
actttattta gtcaaaaaat tagcctttta attctgctgt aacccgtaca tgcccaaaat     120
agggggcggg ttacacagaa tatataacat cgtaggtgtc tgggtgaaca gtttattcct     180
ggcatccact aaatataatg gagcccgctt tttaagctgg catccagaaa aaaaagaat     240
cccagcacca aaatattgtt ttcttcacca accatcagtt cataggtcca ttctcttagc     300
```

```
gcaactacag agaacagggg cacaaacagg caaaaaacgg gcacaacctc aatggagtga    360
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taaagacggt    540
aggtattgat tgtaattctg taaatctatt tcttaaactt cttaaattct acttttatag    600
ttagtctttt ttttagtttt aaaacaccaa gaacttagtt tcgaataaac acacataaac    660
aaacaaa                                                              667

<210> SEQ ID NO 8
<211> LENGTH: 705
<212> TYPE: DNA
<213> ORGANISM: Saccharomyces cerevisiae

<400> SEQUENCE: 8
atccttttgt tgtttccggg tgtacaatat ggacttcctc tttctggca accaaaccca     60 tacatcggga ttcctataat accttcgttg gtctccctaa catgtaggtg gcggagggga   120
gatatacaat agaacagata ccagacaaga cataatgggc taaacaagac tacaccaatt   180
acactgcctc attgatggtg gtacataacg aactaatact gtagccctag acttgatagc   240
catcatcata tcgaagtttc actacccttt ttccatttgc catctattga agtaataata   300
ggcgcatgca acttctttc ttttttttc tttctctct ccccgttgt tgtctcacca       360 tatccgcaat gacaaaaaaa tgatggaaga cactaaagga aaaaattaac gacaaagaca   420
gcaccaacag atgtcgttgt tccagagctg atgaggggta tctcgaagca cacgaaactt   480
tttccttcct tcattcacgc acactactct ctaatgagca acggtatacg gccttccttc   540
cagttacttg aatttgaaat aaaaaaaagt ttgctgtctt gctatcaagt ataaatagac   600
ctgcaattat taatcttttg tttcctcgtc attgttctcg ttccctttct tccttgtttc   660
tttttctgca caatatttca agctatacca agcatacaat caact                   705
```